United States Patent
Gutterer

Patent Number: 6,127,378
Date of Patent: Oct. 3, 2000

[54] PHENANTHRIDINES SUBSTITUTED IN THE 6 POSITION

[75] Inventor: Beate Gutterer, Allensbach, Germany

[73] Assignee: Byk Gulden Lomberg Chemische Fabrik GmbH, Kondtanz, Germany

[21] Appl. No.: 09/142,206

[22] PCT Filed: Mar. 24, 1997

[86] PCT No.: PCT/EP97/01487

§ 371 Date: Sep. 3, 1998

§ 102(e) Date: Sep. 3, 1998

[87] PCT Pub. No.: WO97/35854

PCT Pub. Date: Oct. 2, 1997

[30] Foreign Application Priority Data

Mar. 26, 1996 [DE] Germany ............ 196 11 922
Apr. 2, 1996 [DE] Germany ............ 196 13 091

[51] Int. Cl.[7] .............. A61K 31/44; C07D 221/12; C07D 221/22; C07D 221/28
[52] U.S. Cl. ............ 514/298; 514/284; 514/287; 514/290; 546/65; 546/74; 546/108; 546/109
[58] Field of Search ................. 546/108, 109, 546/65, 74; 514/298, 290, 287, 284

[56] References Cited

FOREIGN PATENT DOCUMENTS 0045171  2/1982  European Pat. Off. .
2144609  2/1973  France .

OTHER PUBLICATIONS

ChemischeBerichte, vol. 103(6), 1970, Weinheim, pp. 1674–1691.
Journal of Liquid Chromatography, vol. 13(3), pp. 543–555, Moriyasu, 1990.
Berichte Der Deutschen Chemischen Gesellschaft, vol. 4, pp. 675–678, Sugasawa, 1939.

Primary Examiner—D. Margaret Seaman
Attorney, Agent, or Firm—Jacobson, Price, Holman & Stern, PLLC

[57] ABSTRACT

Compounds of the formula I

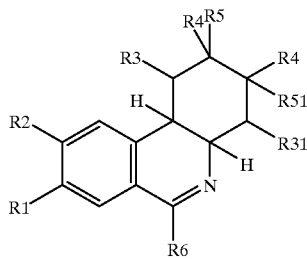

in which R1, R2, R3, R31, R4, R5, R51 and R6 have the meanings indicated in the description, are novel efficacious bronchial therapeutics.

12 Claims, 1 Drawing Sheet

Formula sheet
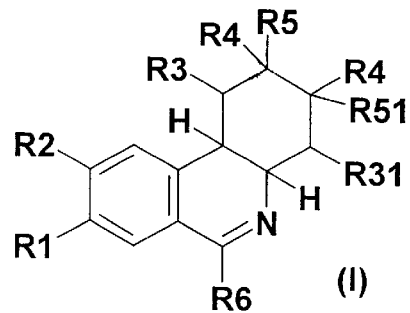
(I)
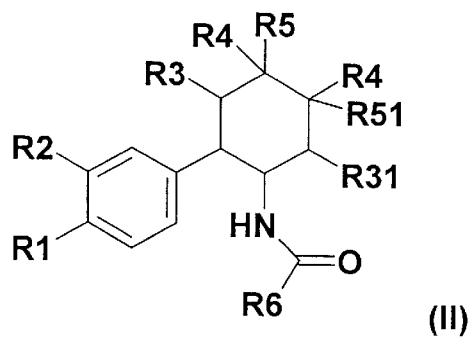
(II)
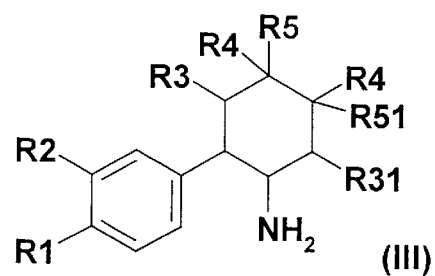
(III)
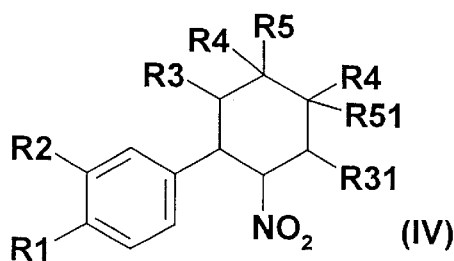
(IV)
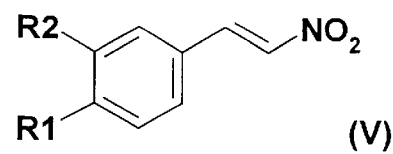
(V)
R3-CH=C(R4)-C(R4)=CH-R31 (VI)
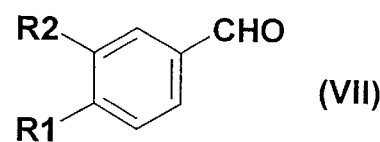
(VII)

PHENANTHRIDINES SUBSTITUTED IN THE 6 POSITION

RELATED APPLICATION

This application has subject matter related to that disclosed and claimed in co-pending application Ser. No. 09/117,507, filed Jul. 31, 1998.

FIELD OF APPLICATION OF THE INVENTION

The invention relates to novel phenanthridines substituted in the 6-position, which are used in the pharmaceutical industry for the production of medicaments.

KNOWN TECHNICAL BACKGROUND

Chem.Ber. 1939, 72, 675–677, J.Chem.Soc., 1956, 4280–4283 and J.Chem.Soc.(C), 1971, 1805 describe the synthesis of 6-phenylphenanthridines.

DESCRIPTION OF THE INVENTION

It has now been found that the novel phenanthridines substituted in the 6-position described in greater detail below have surprising and particularly advantageous properties.

The invention thus relates to compounds of the formula I (I)

in which $R1$ is hydroxyl, 1–4C-alkoxy, 3–7C-cycloalkoxy, 3–7C-cycloalkylmethoxy or 1–4C-alkoxy which is completely or partially substituted by fluorine, $R2$ is hydroxyl, 1–4C-alkoxy, 3–7C-cycloalkoxy, 3–7C-cycloalkylmethoxy or 1–4C-alkoxy which is completely or partially substituted by fluorine, or in which $R1$ and $R2$ together are a 1–2C-alkylenedioxy group, $R3$ is hydrogen or 1–4C-alkyl, $R31$ is hydrogen or 1–4C-alkyl, or in which $R3$ and $R31$ together are a 1–4C-alkylene group, $R4$ is hydrogen or 1–4C-alkyl, $R5$ is hydrogen, $R51$ is hydrogen, or in which $R5$ and $R51$ together are an additional bond, $R6$ is a pyridyl radical which is substituted by $R61$ or a phenyl radical which is substituted by $R7$ and $R8$, where $R61$ is hydrogen, hydroxyl, halogen, 1–4C-alkoxy, 1–4C-alkyl, carboxyl, trifluoromethyl, 1–4C-alkoxycarbonyl or 1–4C-alkoxy which is completely or partially substituted by fluorine, $R7$ is hydroxyl, halogen, cyano, 1–4C-alkyl, 1–4C-alkoxy, 1–4C-alkylcarbonyloxy, trifluoromethyl, phenyl, phenyl-1–4C-alkyl, nitro, amino, 1–4C-alkoxy which is completely or partially substituted by fluorine, or is $SO_2$-$R70$ or $N(R71)R72$, where $R70$ is 1–4C-alkyl, $R71$ is hydrogen, 1–4C-alkyl, $SO_2$-$R9$ or $SO_2$-$R10$ and $R72$ is 1–4-C-alkyl, 1–4C-alkylcarbonyl or $SO_2$-$R10$, $R8$ is hydrogen, hydroxyl, halogen, 1–4C-alkoxy or 1–4C-alkyl and where $R9$ and $R10$ independently of one another are 1–4C-alkyl, phenyl, phenyl-1–4C-alkyl or phenyl which is substituted by one or more identical or different substituents, where the substituents are selected from the group consisting of nitro, 1–4C-alkyl, halogen, 1–4C-alkylcarbonylamino, 1–4C-alkoxy, 1–4C-alkoxy which is completely or partially substituted by fluorine, cyano, phenyl, naphthyl, trifluoromethyl and 1–4C-alkoxycarbonyl, and the salts of these compounds.

1–4C-Alkoxy represents radicals which, in addition to the oxygen atom, contain a straight-chain or branched alkyl radical having 1 to 4 carbon atoms. Examples which may be mentioned are the butoxy radical, isobutoxy radical, sec-butoxy radical, tert-butoxy radical, propoxy radical, isopropoxy radical and preferably the ethoxy radical and methoxy radical.

3–7C-Cycloalkoxy represents, for example, cyclopropyloxy, cyclobutyloxy, cyclopentyloxy, cyclohexyloxy and cycloheptyloxy, of which cyclopropyloxy, cyclobutyloxy and cyclopentyloxy are preferred.

3–7C-Cycloalkylmethoxy represents, for example, cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

Examples which may be mentioned of 1–4C-alkoxy which is completely or partially substituted by fluorine are the 1,2,2-trifluoroethoxy radical, the 2,2,3,3,3-pentafluoropropoxy radical, the perfluoroethoxy radical, the 1,1,2,2-tetrafluoroethoxy radical, the trifluoromethoxy radical, in particular the 2,2,2-trifluoroethoxy radical and preferably the difluoromethoxy radical.

1–4C-Alkyl represents a straight-chain or branched alkyl radical having 1 to 4 carbon atoms. Examples which may be mentioned are the butyl radical, isobutyl radical, sec-butyl radical, tert-butyl radical, propyl radical, isopropyl radical and preferably the ethyl radical and methyl radical.

1–2C-Alkylenedioxy represents, for example, the methylenedioxy radical (—O—$CH_2$—O—) and the ethylenedioxy radical (—O—$CH_2$—$CH_2$—O—).

If $R3$ and $R31$ together have the meaning 1–4C-alkylene, the positions 1 and 4 in compounds of the formula I are linked to one another by a 1–4C-alkylene bridge, 1–4C-alkylene representing straight-chain or branched alkylene radicals having 1 to 4 carbon atoms. Examples which may be mentioned are the radicals methylene (—$CH_2$—), ethylene (—$CH_2$—$CH_2$—), trimethylene (—$CH_2$—$CH_2$—$CH_2$—), 1,2-dimethylethylene [—$CH(CH_3)$—$CH(CH_3)$—] and isopropylidene [—$C(CH_3)_2$—].

Halogen within the meaning of the present invention is bromine, chlorine and fluorine.

In addition to the carbonyl group, 1–4C-alkoxycarbonyl contains one of the abovementioned 1–4C-alkoxy radicals. Examples which may be mentioned are the methoxycarbonyl radical and the ethoxycarbonyl radical.

If $R5$ and $R51$ together are an additional bond, then the carbon atoms in the positions 2 and 3 in compounds of the formula I are linked to one another via a double bond.

In addition to the carbonyloxy radical, 1–4C-alkylcarbonyloxy radicals contain one of the abovementioned 1–4C-alkyl radicals. An example which may be mentioned is the acetyloxy radical (CH$_3$CO—O—).

Phenyl-1–4C-alkyl represents one of the abovementioned 1–4C-alkyl radicals which is substituted by a phenyl radical. Examples which may be mentioned are the benzyl radical and the phenethyl radical.

1–4C-Alkylcarbonyl represents a radical which, in addition to the carbonyl radical, contains one of the abovementioned 1–4C-alkyl radicals. An example which may be mentioned is the acetyl radical.

1–4C-Alkylcarbonylamino represents an amino radical which is substituted by one of the abovementioned 1–4C-alkylcarbonyl radicals. An example which may be mentioned is the acetylamino radical (CH$_3$CO—NH—).

Exemplary pyridyl radicals substituted by R61 which may be mentioned are the radicals pyrid-4-yl, pyrid-3-yl, 2-chloropyrid-4-yl, 2-hydroxypyrid-4-yl, 2-methoxypyrid-4-yl, 2-bromopyrid-4-yl, 2-methylpyrid-4-yl, 3-bromopyrid-4-yl, 2-chloropyrid-5-yl, 2-hydroxypyrid-5-yl, 2-methoxypyrid-5-yl, 2-methylpyrid-5-yl, 2-bromopyrid-5-yl, 3-bromopyrid-5-yl, 2-methylpyrid-3-yl, 2-chloropyrid-3-yl, 4-methylpyrid-3-yl, 3-methoxypyrid-5-yl, 2-(2,2,2-trifluoroethoxy)pyrid-3-yl, 3-methylpyrid-4-yl, 2-methoxypyrid-3-yl, 2-fluoropyrid-3-yl, 2-trifluoromethylpyrid-3-yl, 2-methoxycarbonylpyrid-3-yl, 4-trifluoromethylpyrid-3-yl, 4-methoxycarbonylpyrid-3-yl or 2-(2,2,2-trifluoroethoxy)pyrid-5-yl.

Exemplary phenyl radicals substituted by R7 and R8 which may be mentioned are the radicals 4-acetamidophenyl, 3-acetamidophenyl, 4-acetoxyphenyl, 3-aminophenyl, 4-aminophenyl, 2-bromophenyl, 4-bromophenyl, 2-chlorophenyl, 3-chlorophenyl, 4-chlorophenyl, 3-bromophenyl, 2,3-dichlorophenyl, 2,4-dichlorophenyl, 2-chloro-4-nitrophenyl, 4-diethylamino-2-methylphenyl, 4-methoxyphenyl, 3-methoxyphenyl, 2-chloro-5-nitrophenyl, 4-chloro-3-nitrophenyl, 2,6-dichlorophenyl, 3,5-dichlorophenyl, 2,5-dichlorophenyl, 2,6-dibromophenyl, 2-cyanophenyl, 3-cyanophenyl, 4-cyanophenyl, 4-diethylaminophenyl, 4-dimethylaminophenyl, 2-fluorophenyl, 4-fluorophenyl, 3-fluorophenyl, 2,4-difluorophenyl, 2,6-difluorophenyl, 2-chloro-6-fluorophenyl, 2-fluoro-5-nitrophenyl, 2-hydroxyphenyl, 3-hydroxyphenyl, 3,4-dichlorophenyl, 4-hydroxyphenyl, 4-hydroxy-3-methoxyphenyl, 2-hydroxy-4-methoxyphenyl, 2,4-di-hydroxyphenyl, 2-methoxyphenyl, 2,3-dimethoxyphenyl, 3,4-dimethoxyphenyl, 2,4-dimethoxy-phenyl, 2-dimethylaminophenyl, 2-methylphenyl, 3-methylphenyl, 4-methylphenyl, 2-chloro-6-methylphenyl, 4-methyl-3-nitrophenyl, 2,4-dimethylphenyl, 2,6-dimethylphenyl, 2,3-dimethylphenyl, 2-nitrophenyl, 3-nitrophenyl, 4-nitrophenyl, 2,4-dinitrophenyl, 3,4-dinitrophenyl, 3,5-dinitrophenyl, 2,6-dinitrophenyl, 4-ethoxyphenyl, 2-trifluoromethylphenyl, 4-trifluoromethylphenyl, 3-trifluoromethylphenyl, 4-(p-nitrophenylsulfonamido) phenyl, 3-(p-toluenesulfonamido)phenyl, 4-(p-toluenesulfonamido)phenyl, 4-(4-ethylphenylsulfonamido) phenyl, 4-bis(p-toluenesulfonyl)aminophenyl, 4-bis(p-nitro-phenyl-sulfonyl)aminophenyl, 3-(p-nitrophenylsulfonamido)phenyl, (N-acetyl-4-p-toluenesulfonamido)phenyl, 4-(benzylsulfonamido)phenyl, 3-(benzylsulfonamido)phenyl, 4-(methylsulfonamido) phenyl, 3-(methylsulfonamido)phenyl, 4-(N-methylmethylsulfonamido)phenyl, 3-(N-methylmethylsulfonamido)phenyl, 4-(3,4-dichlorophenylsulfonamido)phenyl, 3-(3,4-dichlorophenylsulfonamido)phenyl, 4-(3-nitrophenylsulfonamido)phenyl, 3-(3-nitrophenylsulfonamido)phenyl, 4-(4-bromophenylsulfonamido)phenyl, 3-(4-bromophenylsulfonamido)phenyl, 4-(3-bromophenylsulfonamido)phenyl, 3-(3-bromophenylsulfonamido)phenyl, 4-(3-fluorophenylsulfonamido)phenyl, 3-(3-fluorophenylsulfonamido)phenyl, 4-(4-fluorophenylsulfonamido)phenyl, 3-(4-fluorophenylsulfonamido)phenyl, 4-(4-chlorophenylsulfonamido)phenyl, 3-(4-chlorophenylsulfonamido)phenyl, 4-(3-chlorophenylsulfonamido)phenyl, 3-(3-chlorophenylsulfonamido)phenyl, 4-(4-acetylaminophenylsulfonamido)phenyl, 3-(4-acetylaminophenylsulfonamido)phenyl, 4-(4-methoxyphenylsulfonamido)phenyl, 3-(4-methoxyphenylsulfonamido)phenyl, 4-(3-trifluoromethylhenylsulfonamido)phenyl, 3-(3-trifluoromethylphenylsulfonamido)phenyl, 4-(4-trifluoromethylphenylsulfonamido)phenyl, 3-(4-trifluoromethylphenylsulfonamido)phenyl, 4-(4-trifluoromethoxyphenylsulfonamido)phenyl, 3-(4-trifluoromethoxyphenylsulfonamido)phenyl, 4-(3-methylphenylsulfonamido)phenyl, 3-(3-methylphenylsulfonamido)phenyl, 4-(3,4-dimethoxyphenylsulfonamido)phenyl, 3-(3,4-dimethoxyphenylsulfonamido)phenyl, 4-(4-cyanophenylsulfonamido)phenyl, 3-(4-cyanophenylsulfonamido)phenyl, 4-(3-cyano-phenylsulfonamido) phenyl, 3-(3-cyanophenylsulfonamido)phenyl, 4-(3-chloro-4-methylphenylsulfonamido)phenyl, 3-(3-chloro-4-methylphenylsulfonamido)phenyl, 4-(4-biphenylsulfonamido)phenyl, 3-(4-biphenylsulfonamido) phenyl, 4-(4-isopropylphenylsulfonamido)phenyl, 3-(4-isopropylphenylsulfonamido)phenyl, 4-(naphth-1-ylsulfonamido)phenyl, 3-(naphth-1-ylsulfonamido)phenyl, 4-(naphth-2-ylsulfonamido)phenyl, 3-(naphth-2-ylsulfonamido)-phenyl, 4-benzylphenyl, 4-biphenyl, 4-trifluoromethoxyphenyl, 3-trifluoromethoxyphenyl, 2-trifluoromethoxyphenyl, 4-methanesulfonylphenyl, 3-methanesulfonylphenyl, 2-methanesulfonylphenyl, 4-(4-methoxycarbonylphenylsulfonamido)phenyl or (N-methyl-4-p-toluenesulfonamido)phenyl.

Compounds of the formula I to be emphasized are those in which

R1 is hydroxyl, 1–4C-alkoxy, 3–7C-cycloalkoxy, 3–7C-cycloalkylmethoxy or 1–4C-alkoxy which is completely or partially substituted by fluorine, R2 is hydroxyl, 1–4C-alkoxy, 3–7C-cycloalkoxy, 3–7C-cycloalkylmethoxy or 1–4C-alkoxy which is completely or partially substituted by fluorine, or in which R1 and R2 together are a 1–2C-alkylenedioxy group, R3 is hydrogen or 1–4C-alkyl, R31 is hydrogen or 1–4C-alkyl, or in which
R3 and R31 together are a 1–4C-alkylene group,
R4 is hydrogen or 1–4C-alkyl,
R5 is hydrogen,
R51 is hydrogen,
or in which
R5 and R51 together are an additional bond,
R6 is a pyridyl radical which is substituted by R61 or a phenyl radical which is substituted by R7 and R8, where
R61 is hydrogen, hydroxyl, halogen, 1–4C-alkoxy, 1–4C-alkyl, carboxyl, trifluoromethyl, 1–4C-alkoxycarbonyl or 1–4C-alkoxy which is completely or partially substituted by fluorine,
R7 is hydroxyl, halogen, cyano, 1–4C-alkyl, 1–4C-alkoxy, 1–4C-alkylcarbonyloxy, trifluoromethyl, phenyl, phenyl-1–4C-alkyl, nitro, amino or N(R71)R72, where
R71 is hydrogen, 1–4C-alkyl, $SO_2$-R9 or $SO_2$-R10 and R72 is 1–4C-alkyl, 1–4C-alkylcarbonyl or $SO_2$-R10,
R8 is hydrogen, hydroxyl, halogen, 1–4C-alkoxy or 1–4C-alkyl,
and where
R9 and R10 independently of one another are 1–4C-alkyl, phenyl, phenyl-1–4C-alkyl or phenyl which is substituted by one or more identical or different substituents, the substituents being selected from the group consisting of nitro, 1–4C-alkyl, halogen, 1–4C-alkylcarbonylamino, 1–4C-alkoxy, 1–4C-alkoxy which is completely or partially substituted by fluorine, cyano, phenyl, naphthyl and trifluoromethyl,
and the salts of these compounds.

An embodiment [embodiment a)] of the compounds according to the invention are compounds of the formula 1, in which
R1 is hydroxyl, 1–4C-alkoxy, 3–7C-cycloalkoxy, 3–7C-cycloalkylmethoxy or 1–4C-alkoxy which is completely or partially substituted by fluorine,
R2 is hydroxyl, 1–4C-alkoxy, 3–7C-cycloalkoxy, 3–7C-cycloalkylmethoxy or 1–4C-alkoxy which is completely or partially substituted by fluorine,
or in which
R1 and R2 together are a 1–2C-alkylenedioxy group,
R3 is hydrogen or 1–4C-alkyl,
R31 is hydrogen or 1–4C-alkyl,
or in which
R3 and R31 together are a 1–4C-alkylene group,
R4 is hydrogen or 1–4C-alkyl,
R5 is hydrogen,
R51 is hydrogen,
or in which
R5 and R51 together are an additional bond,
R6 is a pyridyl radical which is substituted by R61, where
R61 is hydrogen, hydroxyl, halogen, 1–4C-alkoxy, 1–4C-alkyl, carboxyl, trifluoromethyl, 1–4C-alkoxycarbonyl or 1–4C-alkoxy which is completely or partially substituted by fluorine,
and the salts of these compounds.

Compounds of embodiment a) to be emphasized are compounds of the formula I in which
R1 is 1–4C-alkoxy, 3–7C-cycloalkoxy, 3–7C-cycloalkylmethoxy or 1–2C-alkoxy which is completely or partially substituted by fluorine,
R2 is 1–4C-alkoxy, 3–7C-cycloalkoxy, 3–7C-cycloalkylmethoxy or 1–2C-alkoxy which is completely or partially substituted by fluorine,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is a pyridyl radical which is substituted by R61, where
R61 is hydrogen, hydroxyl, halogen or 1–4C-alkoxy,
and the salts of these compounds.

Compounds of embodiment a) particularly to be emphasized are compounds of the formula I in which
R1 is 1–4C-alkoxy, 3–7C-cycloalkoxy or 1–2C-alkoxy which is completely or partially substituted by fluorine,
R2 is 1–4C-alkoxy, 3–7C-cycloalkoxy or 1–2C-alkoxy which is completely or partially substituted by fluorine,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is a pyridyl radical which is substituted by R61, where
R61 is hydrogen, hydroxyl, halogen or 1–4C-alkoxy,
and the salts of these compounds.

Preferred compounds of embodiment a) are compounds of the formula I in which
R1 is 1–4C-alkoxy,
R2 is 1–4C-alkoxy,
R3 is hydrogen,
R31 is hydrogen,
R4 is hydrogen,
R5 is hydrogen,
R51 is hydrogen,
R6 is a pyridyl radical which is substituted by R61, where
R61 is hydrogen, hydroxyl or halogen,
and the salts of these compounds.

Another embodiment [embodiment b)] of the compounds according to the invention are those compounds of the formula I in which
R1 is hydroxyl, 1–4C-alkoxy, 3–7C-cycloalkoxy, 3–7C-cycloalkylmethoxy or 1–4C-alkoxy which is completely or partially substituted by fluorine,
R2 is hydroxyl, 1–4C-alkoxy, 3–7C-cycloalkoxy, 3–7C-cycloalkylmethoxy or 1–4C-alkoxy which is completely or partially substituted by fluorine,
or in which
R1 and R2 together are a 1–2C-alkylenedioxy group,
R3 is hydrogen or 1–4C-alkyl,
R31 is hydrogen or 1–4C-alkyl, or in which
- R3 and R31 together are a 1–4C-alkylene group,
- R4 is hydrogen or 1–4C-alkyl,
- R5 is hydrogen,
- R51 is hydrogen, or in which
- R5 and R51 together are an additional bond,
- R6 is a phenyl radical which is substituted by R7 and R8, where
  - R7 is hydroxyl, halogen, cyano, 1–4C-alkyl, 1–4C-alkoxy, 1–4C-alkylcarbonyloxy, trifluoromethyl, phenyl, phenyl-1–4C-alkyl, nitro, amino or N(R71)R72, where
    - R71 is hydrogen, 1–4C-alkyl, SO$_2$-R9 or SO$_2$-R10 and
    - R72 is 1–4C-alkyl, 1–4C-alkylcarbonyl or SO$_2$-R10,
  - R8 is hydrogen, hydroxyl, halogen, 1–4C-alkoxy or 1–4C-alkyl and where
  - R9 and R10 independently of one another are 1–4C-alkyl, phenyl, phenyl-1–4C-alkyl or phenyl which is substituted by one or more identical or different substituents, the substituents being selected from the group consisting of nitro, 1–4C-alkyl, halogen, 1–4C-alkylcarbonylamino, 1–4C-alkoxy, 1–4C-alkoxy which is completely or partially substituted by fluorine, cyano, phenyl, naphthyl and trifluoromethyl, and the salts of these compounds.

Compounds of embodiment b) to be emphasized are compounds of the formula I in which
- R1 is 1–4C-alkoxy, 3–7C-cycloalkoxy, 3–7C-cycloalkylmethoxy or 1–2C-alkoxy which is completely or partially substituted by fluorine,
- R2 is 1–4C-alkoxy, 3–7C-cycloalkoxy, 3–7C-cycloalkylmethoxy or 1–2C-alkoxy which is completely or partially substituted by fluorine,
- R3 is hydrogen,
- R31 is hydrogen, or in which
- R3 and R31 together are a 1–4C-alkylene group,
- R4 is hydrogen or 1–4C-alkyl,
- R5 is hydrogen,
- R51 is hydrogen, or in which
- R5 and R51 together are an additional bond,
- R6 is a phenyl radical which is substituted by R7 and R8, where
  - R7 is hydroxyl, halogen, 1–4C-alkyl, 1–4C-alkoxy, 1–4C-alkylcarbonyloxy, trifluoromethyl, phenyl, phenyl-1–4C-alkyl, nitro, amino or N(R71)R72, where
    - R71 is hydrogen, 1–4C-alkyl, SO$_2$-R9 or SO$_2$-R10 and
    - R72 is 1–4C-alkyl, 1–4C-alkylcarbonyl or SO$_2$-R10,
  - R8 is hydrogen, hydroxyl, halogen, 1–4C-alkoxy or 1–4C-alkyl and where
- R9 and R10 independently of one another are 1–4C-alkyl, phenyl or phenyl which is substituted by a substituent, the substituent being selected from the group consisting of nitro, 1–4C-alkyl, halogen and trifluoromethyl, and the salts of these compounds.

Compounds of embodiment b) particularly to be emphasized are compounds of the formula I in which
- R1 is 1–4C-alkoxy, 3–7C-cycloalkoxy or 1–2C-alkoxy which is completely or partially substituted by fluorine,
- R2 is 1–4C-alkoxy, 3–7C-cycloalkoxy or 1–2C-alkoxy which is completely or partially substituted by fluorine,
- R3 is hydrogen,
- R31 is hydrogen, or in which
- R3 and R31 together are a 1–4C-alkylene group,
- R4 is hydrogen or 1–4C-alkyl,
- R5 is hydrogen,
- R51 is hydrogen, or in which
- R5 and R51 together are an additional bond,
- R6 is a phenyl radical which is substituted by R7 and R8, where
  - R7 is hydroxyl, halogen, 1–4C-alkoxy, 1–4C-alkylcarbonyloxy, phenyl, phenyl-1–4C-alkyl, nitro, amino or N(R71)R72, where
    - R71 is hydrogen, SO$_2$-R9 or SO$_2$-R10 and
    - R72 is 1–4C-alkylcarbonyl or SO$_2$-R10,
  - R8 is hydrogen, halogen or 1–4C-alkoxy and where
- R9 and R10 independently of one another are phenyl or phenyl which is substituted by a substituent, the substituent being selected from the group consisting of nitro, 1–4C-alkyl, halogen and trifluoromethyl, and the salts of these compounds.

Preferred compounds of embodiment b) are compounds of the formula I in which
- R1 is 1–4C-alkoxy or 3–7C-cycloalkoxy,
- R2 is 1–4C-alkoxy or 3–7C-cycloalkoxy,
- R3 is hydrogen,
- R31 is hydrogen, or in which
- R3 and R31 together are a 1–2C-alkylene group,
- R4 is hydrogen or 1–4C-alkyl,
- R5 is hydrogen,
- R51 is hydrogen, or in which
- R5 and R51 together are an additional bond,
- R6 is a phenyl radical which is substituted by R7 and R8, where
  - R7 is hydroxyl, halogen, 1–4C-alkoxy, 1–4C-alkylcarbonyloxy, phenyl, phenyl-1–4C-alkyl, nitro, amino or N(R71)R72, where
    - R71 is hydrogen or SO$_2$-R10 and
    - R72 is 1–4C-alkylcarbonyl or SO$_2$-R10,
  - R8 is hydrogen, halogen or 1–4C-alkoxy and where
- R10 is phenyl which is substituted by a substituent, the substituent being selected from the group consisting of nitro and 1–4C-alkyl, and the salts of these compounds.

An embodiment [embodiment c)] of the compounds according to the invention are those compounds of the formula I in which
- R1 is hydroxyl, 1–4C-alkoxy, 3–7C-cycloalkoxy, 3–7C-cycloalkylmethoxy or 1–4C-alkoxy which is completely or partially substituted by fluorine,
- R2 is hydroxyl, 1–4C-alkoxy, 3–7C-cycloalkoxy, 3–7C-cycloalkylmethoxy or 1–4C-alkoxy which is completely or partially substituted by fluorine, or in which
R1 and R2 together are a 1–2C-alkylenedioxy group,
R3 is hydrogen or 1–4C-alkyl,
R31 is hydrogen or 1–4C-alkyl,
or in which
R3 and R31 together are a 1–4C-alkylene group,
R4 is hydrogen or 1–40-alkyl,
R5 is hydrogen,
R51 is hydrogen,
or in which
R5 and R51 together are an additional bond,
R6 is a phenyl radical which is substituted by R7 and R8, where
R7 is hydroxyl, halogen, cyano, 1–4C-alkyl, 1–4C-alkoxy, 1–4C-alkylcarbonyloxy, trifluoromethyl, phenyl, phenyl-1–4C-alkyl, nitro, amino, 1–4C-alkoxy which is completely or partially substituted by fluorine, or is $SO_2$-R70 or N(R71)R72, where
R70 is 1–4C-alkyl,
R71 is hydrogen, 1–4C-alkyl, $SO_2$-R9 or $SO_2$-R10 and
R72 is 1–4C-alkyl, 1–4C-alkylcarbonyl or $SO_2$-R10,
R8 is hydrogen, hydroxyl, halogen, 1–4C-alkoxy or 1–4C-alkyl
and where
R9 and R10 independently of one another are 1–4C-alkyl, phenyl, phenyl-1–4C-alkyl or phenyl which is substituted by one or more identical or different substituents, the substituents being selected from the group consisting of nitro, 1–4C-alkyl, halogen, 1–4C-alkylcarbonylamino, 1–4C-alkoxy, 1–4C-alkoxy which is completely or partially substituted by fluorine, cyano, phenyl, naphthyl, trifluoromethyl and 1–4C-alkoxycarbonyl,
and the salts of these compounds.
Compounds of embodiment c) to be emphasized are those compounds of the formula I in which
R1 is 1–4C-alkoxy, 3–7C-cycloalkoxy, 3–7C-cycloalkylmethoxy or 1–2C-alkoxy which is completely or partially substituted by fluorine,
R2 is 1–4C-alkoxy, 3–7C-cycloalkoxy, 3–7C-cycloalkylmethoxy or 1–2C-alkoxy which is completely or partially substituted by fluorine,
R3 is hydrogen,
R31 is hydrogen,
or in which
R3 and R31 together are a 1–4C-alkylene group,
R4 is hydrogen or 1–4C-alkyl,
R5 is hydrogen,
R51 is hydrogen,
or in which
R5 and R51 together are an additional bond,
R6 is a phenyl radical which is substituted by R7 and R8, where
R7 is hydroxyl, halogen, cyano, 1–4C-alkyl, 1–4C-alkoxy, 1–4C-alkylcarbonyloxy, trifluoromethyl, phenyl, phenyl-1–4C-alkyl, nitro, amino, 1–4C-alkoxy which is completely or partially substituted by fluorine, or is $SO_2$-R70 or N(R71)R72, where
R70 is 1–4C-alkyl,
R71 is hydrogen, 1–4C-alkyl, $SO_2$-R9 or $SO_2$-R10 and
R72 is 1–4C-alkyl, 1–4C-alkylcarbonyl or $SO_2$-R10,
R8 is hydrogen, hydroxyl, halogen, 1-4C-alkoxy or 1–4C-alkyl
and where
R9 and R10 independently of one another are 1–4C-alkyl, phenyl or phenyl which is substituted by a substituent, the substituent being selected from the group consisting of nitro, 1–4C-alkyl, halogen, trifluoromethyl and 1 –4C-alkoxycarbonyl, and the salts of these compounds.
Compounds of embodiment c) particularly to be emphasized are those compounds of the formula I in which
R1 is 1–4C-alkoxy, 3–7C-cycloalkoxy or 1–2C-alkoxy which is completely or partially substituted by fluorine,
R2 is 1–4C-alkoxy, 3–7C-cycloalkoxy or 1–2C-alkoxy which is completely or partially substituted by fluorine,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is a phenyl radical which is substituted by R7 and R8, where
R7 is hydroxyl, halogen, cyano, 1–4C-alkoxy, 1–4C-alkylcarbonyloxy, trifluoromethyl, phenyl, phenyl-1–4C-alkyl, nitro, amino, 1–4C-alkoxy which is completely or partially substituted by fluorine, or is $SO_2$-R70 or N(R71)R72, where
R70 is 1–4C-alkyl,
R71 is hydrogen, 1–4C-alkyl, $SO_2$-R9 or $SO_2$-R10 and
R72 is 1–4C-alkylcarbonyl or $SO_2$-R10,
R8 is hydrogen, halogen or 1–4C-alkoxy
and where
R9 and R10 independently of one another are phenyl or phenyl which is substituted by a substituent, the substituent being selected from the group consisting of nitro, 1–4C-alkyl, halogen, trifluoromethyl and 1–4C-alkoxycarbonyl,
and the salts of these compounds.
Preferred compounds of embodiment c) are those compounds of the formula I in which
R1 is 1–4C-alkoxy or 3–7C-cycloalkoxy,
R2 is 1–4C-alkoxy or 3–7C-cycloalkoxy,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is a phenyl radical which is substituted by R7 and R8, where
R7 is hydroxyl, halogen, cyano, 1–4C-alkoxy, 1–4C-alkylcarbonyloxy, trifluoromethyl, phenyl, phenyl-1–4C-alkyl, nitro, amino, 1–4C-alkoxy which is completely or partially substituted by fluorine, or is $SO_2$-R70 or N(R71 )R72, where
R70 is 1–4C-alkyl,
R71 is hydrogen, 1–4C-alkyl or $SO_2$-R10 and
R72 is 1–4C-alkylcarbonyl or $SO_2$-R10,
R8 is hydrogen, halogen or 1–4C-alkoxy
and where
R10 is phenyl which is substituted by a substituent, the substituent being selected from the group consisting of nitro, 1–4C-alkyl and 1–4C-alkoxycarbonyl, and the salts of these compounds.

Particularly preferred compounds of the formula I are those in which

R1 is 1–4C-alkoxy or 3–7C-cycloalkoxy,
R2 is 1–4C-alkoxy or 3–7C-cycloalkoxy,
R3 is hydrogen,
R31 is hydrogen,
R4 is hydrogen or 1–4C-alkyl,
R5 is hydrogen,
R51 is hydrogen, or in which R5 and R51 together are an additional bond,
R6 is a phenyl radical which is substituted by R7 and R8, where
  R7 is N(R71)R72, where
    R71 is hydrogen, SO$_2$-R9 or SO$_2$-R10 and
    R72 is 1–4C-alkyl, 1–4C-alkylcarbonyl or SO$_2$-R10,
  R8 is hydrogen
and where
  R9 and R10 independently of one another are phenyl which is substituted by a substituent, the substituents being selected from the group consisting of nitro, 1–4C-alkyl and 1–4C-alkoxycarbonyl,
and the salts of these compounds.

Suitable salts for compounds of the formula I—depending on substitution—are all acid addition salts or salts with bases. Particular mention may be made of the pharmacologically tolerable salts of the inorganic and organic acids and bases customarily used in pharmacy. Those suitable are, on the one hand, water-soluble and water-insoluble acid addition salts with acids such as hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed in salt preparation—depending on whether it is a mono- or polybasic acid and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here, too, the bases are employed in salt preparation in an equimolar quantitative ratio or one differing therefrom.

Pharmacologically intolerable salts which can initially be obtained, for example, as process products in the preparation of the compounds according to the invention on an industrial scale, are converted into pharmacologically tolerable salts by processes known to the person skilled in the art.

The compounds of the formula I are chiral compounds having chiral centers in positions 4a and 10b and, depending on the meaning of the substituents R3, R31, R4, R5 and R51, further chiral centers in positions 1, 2, 3 and 4. The invention therefore includes all conceivable pure diastereomers and pure enantiomers and their mixtures in any mixing ratio, including the racemates. The compounds of the formula I are preferred in which the hydrogen atoms in the positions 4a and 10b are cis to one another. The pure cis diastereomers and the pure cis enantiomers are particularly preferred in this case, and their mixtures in any mixing ratio and including the racemates.

The enantiomers can be separated in a manner known per se (for example by preparation and separation of corresponding diastereoisomeric compounds). A resolution of enantiomers is preferably carried out at the stage of the starting compounds of the formula III (see attached formula sheet), for example via salt formation of the racemic compounds of the formula III with optically active carboxylic acids. Alternatively, enantiomerically pure starting compounds of the formula III can also be prepared by means of asymmetric syntheses.

The invention further relates to a process for the preparation of the compounds of the formula 1, in which R1, R2, R3, R31, R4, R5, R51 and R6 have the meanings indicated above, and their salts. The process comprises a) cyclocondensing appropriate compounds of the formula II

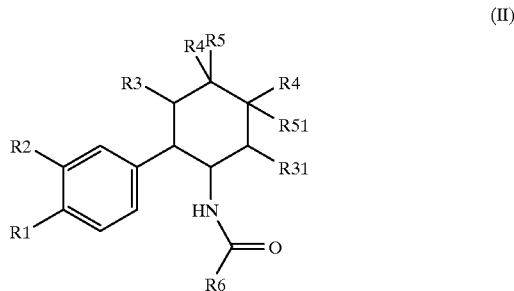

in which R1, R2, R3, R31, R4, R5, R51 and R6 have the meanings indicated above, or b) for the preparation of compounds of the formula I in which R1, R2, R3, R31, R4, R5 and R51 have the meanings indicated above and R6 is pyridyl substituted by R61, where R61 is hydroxyl, hydrolyzing appropriate compounds of the formula I in which R1, R2, R3, R31, R4, R5 and R51 have the meanings indicated above and R6 is pyridyl substituted by R61, where R61 is halogen, or c) for the preparation of compounds of the formula I in which R1, R2, R3, R31, R4, R5 and R51 have the abovementioned meanings and R6 is a phenyl radical which is substituted by R7 and R8, where R7 is amino, reducing corresponding compounds of the formula I in which R7 is nitro, or d) for the preparation of compounds of the formula I in which R1, R2, R3, R31, R4, R5 and R51 have the abovementioned meanings and R6 is a phenyl radical which is substituted by R7 and R8, where R7 is hydroxyl, hydrolyzing corresponding compounds of the formula I in which R7 is 1–4C-alkylcarbonyloxy, or e) N-acylating compounds of the formula I in which R1, R2, R3, R31, R4, R5 and R51 have the abovementioned meanings and R6 is a phenyl radical which is substituted by R7 and R8, where R7 is amino, with a suitably activated 1–4C-alkylcarbonyl derivative, or f) reacting compounds of the formula I in which R1, R2, R3, R31, R4, R5 and R51 have the abovementioned meanings and R6 is a phenyl radical which is substituted by R7 and R8, where R7 is amino, with a sulfonic acid compound of the formula X-SO$_2$-R10, in which R10 has the abovementioned meaning and X is a suitable leaving group, or g) N-acylating compounds of the formula I in which R1, R2, R3, R31, R4, R5 and R51 have the abovementioned meanings and R6 is a phenyl radical which is substituted by R7 and R8, where R7 is the group N(H)R72, where R72 has the meaning 1–4C-alkylcarbonyl or $SO_2$-R10, with a suitably activated 1–4C-alkylcarbonyl derivative, N-alkylating with a suitably activated 1–4C-alkyl derivative or reacting with a sulfonic acid compound of the formula X-$SO_2$-R9 or X-$SO_2$-R10, in which R9 and R10 have the abovementioned meanings and X is a suitable leaving group, and, if desired, then converting compounds of the formula I obtained according to a), b), c), d), e), f) or g) into their salts, or, if desired, then converting salts of the compounds of the formula I obtained according to a), b), c), d), e), f) or g) into the free compounds.

The cyclocondensation according to process variant a) is carried out in a manner known per se to the person skilled in the art according to Bischler-Napieralski (e.g. as described in J.Chem.Soc., 1956, 4280–4282) in the presence of a suitable condensing agent, such as, for example, polyphosphoric acid, phosphorus pentachloride, phosphorus pentoxide or preferably phosphorus oxytrichloride, in a suitable inert solvent, e.g. in a chlorinated hydrocarbon such as chloroform, or in a cyclic hydrocarbon such as toluene or xylene, or another inert solvent such as acetonitrile, or without further solvent using an excess of condensing agent, preferably at elevated temperature, in particular at the boiling temperature of the solvent or condensing agent used.

The hydrolysis of compounds of the formula I in which R61 is halogen, in particular bromine or chlorine, according to variant b) is likewise carried out in a manner known to the person skilled in the art (e.g. as described in Helv.Chim.Acta 1942, 25, 1485), in a suitable solvent and in the presence or absence of water, by reaction with one or more suitable bases, at reaction temperatures between 0° C. and the boiling temperature of the solvent used.

Suitable bases are, for example, metal carbonates such as potassium and sodium carbonate and metal hydroxides, such as potassium and sodium hydroxide, a combination of metal carbonate and metal hydroxide preferably being used when conducting the reaction with exclusion of water. If desired, when using an organic solvent, the conduct of the reaction can be improved by addition of a complexing reagent (e.g. as described in Tetrahedron 1987, 43, 2557).

The reduction of the nitro compounds analogously to variant c) is expediently carried out by catalytic hydrogenation, for example using Raney nickel and molecular hydrogen or another hydrogen source such as hydrazine, using base metals such as tin, zinc and iron (preferably in acidic solution), electrolytically or using other suitable reductants, in a suitable solvent, e.g. in water or an alcohol, such as methanol or ethanol and, if desired, in the presence of an acid such as, hydrochloric acid.

Reduction with iron and hydrochloric acid, e.g. as described in the examples, is particularly preferred.

Hydrolysis according to variant d) is likewise carried out in a manner known to the person skilled in the art, preferably under basic conditions, for example using a base such as potassium hydroxide in a suitable solvent, e.g. an alcohol such as methanol, and in the presence or absence of water.

N-Acylation according to variant e) is carried out in a manner as is known for the preparation of amides. Suitably activated 1–4C-alkylcarbonyl derivatives are, for example, corresponding acids, esters, azides and in particular anhydrides and halides (preferably chlorides and bromides).

If desired, the reaction can be carried out in the presence of a suitable base, e.g. of an alkali metal carbonate such as potassium carbonate, of an alkali metal hydroxide such as sodium hydroxide or of a nitrogen base such as pyridine, triethylamine or ethyldiisopropylamine and/or employing an excess of amine of the formula I. Alternatively, the reaction can also be carried out without base, where—depending on the nature of the starting compounds—if appropriate the acid addition salts can first be separated off in particularly pure form.

Suitable solvents which may be mentioned for the acylation are solvents, such as dimethyl sulfoxide, acetone, tetrahydrofuran, dimethylformamide or acetonitrile, or alternatively chlorinated hydrocarbons, such as methylene chloride. If desired, the reaction can also be carried out without additional solvent using an excess of acylating agent and/or base as the solvent.

The preparation of sulfonamides of the formula I according to the invention according to variant f) is carried out in a manner as is known for the synthesis of sulfonamides, for example analogously to the N-acylation according to variant e). Preferred sulfonic acid derivatives of the formula X-$SO_2$-R10 which are used in this case are those in which X is a suitable leaving group such as, for example, halogen, in particular chlorine.

Depending on whether compounds of the formula I in which R7 is N(H)$SO_2$-R10 or N($SO_2$-R10)$_2$ are the desired product, the sulfonic acid derivative of the formula X-$SO_2$-R10 is employed in an equimolar quantitative ratio or one differing therefrom.

The reaction according to variant g) can likewise be carried out in a manner known to the person skilled in the art, for example analogously to variant e) or f). The compounds of the formula I in which R7 is the group N(H)R72, where R72 has the meaning 1–4C-alkylcarbonyl or $SO_2$-R10, can in this case be employed as such or preferably in the form of their salts with bases, e.g. in the form of the alkali metal salts (in particular as the sodium salt). Expediently, the salt is produced from the corresponding free compounds of the formula I immediately before the reaction by deprotonation using a suitable base, for example using a metal hydride such as sodium hydride, in a preferably aprotic dipolar solvent such as dimethylformamide or tetrahydrofuran.

The substances according to the invention are isolated and purified in a manner known per se, e.g. by distilling off the solvent in vacuo and recrystallizing the resulting residue from a suitable solvent or subjecting it to one of the customary purification methods, such as column chromatography on suitable support material.

Salts are obtained by dissolving the free compound in a suitable solvent, e.g. a chlorinated hydrocarbon, such as methylene chloride or chloroform, or a low molecular weight aliphatic alcohol (ethanol, isopropanol) which contains the desired acid or base, or to which the desired acid or base is then added. The salts are obtained by filtering, reprecipitating, precipitating using a nonsolvent for the addition salt or by evaporation of the solvent. Salts obtained can be converted by alkalization or by acidification into the free compounds, which in turn can be converted into salts. In this manner, pharmacologically intolerable salts can be converted into pharmacologically tolerable salts.

Compounds of the formula II

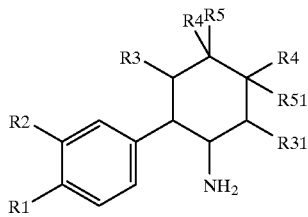
(III)

in which R1, R2, R3, R31, R4, R5, R51 and R6 have the meanings indicated above are accessible from the corresponding compounds of the formula III (see attached formula sheet) in which R1, R2, R3, R31, R4, R5 and R51 have the meanings indicated above, by reaction with compounds of the formula R6-CO-X, in which R6 has the meaning indicated above and X is a suitable leaving group, preferably a chlorine atom. For example, the acylation or benzoylation is carried out as described in the following examples or as in J.Chem. Soc.(C), 1971, 1805–1808.

Compounds of the formula R6-CO-X and compounds of the formula III are either known or can be prepared in a known manner.

The compounds of the formula III can be prepared from compounds of the formula IV

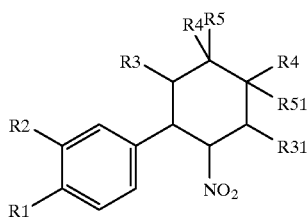
(IV)

in which R1, R2, R3, R31, R4, R5 and R51 have the abovementioned meanings, by reduction of the nitro group.

Reduction is carried out in a manner known to the person skilled in the art, for example as described in J.Org.Chem. 1962, 27, 4426 or as described in the following examples. Preferably, the reduction is carried out by catalytic hydrogenation, e.g. in the presence of Raney nickel, in a lower alcohol such as methanol or ethanol at room temperature and at normal or elevated pressure. If desired, a catalytic amount of an acid, such as, for example, hydrochloric acid, can be added to the solvent.

The compounds of the formula IV in which R1, R2, R3, R31 and R4 have the meanings indicated above and R5 and R51 are hydrogen, are either known or can be prepared from corresponding compounds of the formula IV in which R5 and R51 together are an additional bond. The reaction can be carried out in a manner known to the person skilled in the art, preferably by hydrogenation in the presence of a catalyst, such as, for example, palladium on active carbon, e.g. as described in J.Chem.Soc.(C), 1971, 1805–1808 or as in the following examples.

The compounds of the formula IV in which R5 and R51 together are an additional bond are either known or can be obtained by reaction of compounds of the formula V

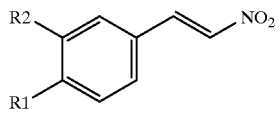
(V)

in which R1 and R2 have the abovementioned meanings, with compounds of the formula VI

R3—CH=C(R4)—C(R4)=CH—R31 (VI)

in which R3, R31 and R4 have the abovementioned meanings.

The cycloaddition is in this case carried out in a manner known to the person skilled in the art according to Diels-Alder, e.g. as described in J.Amer.Chem.Soc. 1957, 79, 6559 or in J.Org.Chem. 1952, 17, 581 or as in the following examples.

Compounds of the formula IV obtained in the cycloaddition, in which the phenyl ring and the nitro group are trans to one another, can be converted into the corresponding cis compounds in a manner known to the person skilled in the art, e.g. as described in J. Amer.Chem.Soc. 1957, 79, 6559 or as in the following examples.

The compounds of the formulae VI and V are either known or can be prepared in a known manner. The compounds of the formula V can be prepared, for example, in a manner known to the person skilled in the art from corresponding compounds of the formula VII, as described, for example, in J.Chem.Soc. 1951, 2524 or in J.Org.Chem. 1944, 9, 170 or as in the following examples.

The compounds of the formula VII

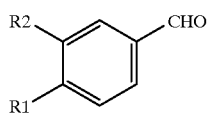
(VII)

in which R1 and R2 have the meanings indicated above are either known or can be prepared in a manner known to the person skilled in the art, as described, for example, in Ber.Dtsch.Chem. Ges. 1925, 58, 203 or as in the following examples.

The following examples serve to illustrate the invention in greater detail without restricting it. Likewise, further compounds of the formula I whose preparation is not explicitly described can be prepared in an analogous manner or in a manner familiar to the person skilled in the art per se using customary process techniques.

In the examples, m.p. stands for melting point, b.p. for boiling point, h for hour(s), RT for room temperature, EF for empirical formula, MW for molecular weight, calc. for calculated, fnd for found. The compounds and their salts mentioned in the examples are a preferred subject of the invention.

EXAMPLES

Final Products 1. (+/−)-cis-8,9-Dimethoxy-6-(4-p-toluenesulfonamidophenyl)-1,2,3,4,4a,10b-hexahydrophenanthridine 3.5 g of (+/−)-cis-N-[2-(3,4-dimethoxyphenyl) cyclohexyl]-4-p-toluenesulfonamidobenzamide are dissolved in 100 ml of acetonitrile and 1.0 ml of phosphorus oxychloride and the solution is stirred at 50° C. for 8 h. The reaction mixture is added to 100 ml of saturated sodium hydrogencarbonate solution and extracted with ethyl acetate. The organic phase is washed with sodium hydrogencarbonate solution and water, dried using sodium sulfate and concentrated. The residue is recrystallized from ethanol. 1.8 g (53.2% of theory) of the title compound of melting point: 122° C. (decomposition) are obtained.

EF: $C_{28}H30M_2O_4S$; MW: 490.63

Elemental analysis: calc.: C 68.54 H 6.16 N 5.71 S 6.53 fnd: C 68.35 H 6.24 N 5.55 S 6.47

Starting from the starting compounds described below, the following are obtained according to the procedure as in Example 1:

2. (+/−)-cis-8,9-Diethoxy-6-(4-p-toluenesulfonamidophenyl)-1,2,3,4,4a,10b-hexahydrophenanthridine M.p.: 110–115° C., yield 42.4% of theory

EF: $C_{30}H_{34}N_2O_4S$; MW: 518.68

Elemental analysis: calc.: C 68.99 H 6.64 N 5.36 S 6.14 fnd: C 69.04 H 6.58 N 5.28 S 6.12

3. (+/−)-cis-9-Cyclopentyloxy-8-methoxy-6-(4-p-toluenesulfonamidophenyl)-1,2,3,4,4a10b-hexahydrophenanthridine M.p.: 175° C., yield 62.5% of theory

EF: $C_{32}H_{36}N_2O_4S$; MW: 544.72

Elemental analysis: calc.: C 70.56 H 6.66 N 5.14 S 5.89 fnd: C 70.09 H 6.72 N 5.05 S 5.88

4. (+/−)-cis-8-Cyclopentyloxy-9-methoxy-6-(4-p-toluenesulfonamidophenyl)-1,2,3,4,4a,10b-hexahydrophenanthridine M.p.: 193–196° C., yield 38.9% of theory

EF: $C_{32}H_{36}N_2O_4S$; MW: 544.72

Elemental analysis: calc.: C 70.56 H 6.66 N 5.14 S 5.89 fnd: C 70.39 H 6.77 N 5.10 S 5.73

5. (+/−)-cis-8,9-Dimethoxy-6-(4-nitrophenyl)-1,2,3,4,4a,10b-hexahydrophenanthridine M.p.: 182° C., yield 75.2% of theory

EF: $C_{21}H_{22}N_2O_4$; MW: 366.42

Elemental analysis: calc.: C 68.84 H 6.05 N 7.65 fnd: C 68.88 H 6.10 N 7.57

6. (+/−)-cis-8,9-Dimethoxy-6-(2,6-dichlorophenyl)-1,2,3,4,4a,10b-hexahydrophenanthridine M.p.: 174–175° C., yield 44.0% of theory

EF: $C_{21}H_{21}C_2NO_2$; MW: 390.31

Elemental analysis: calc.: C 64.62 H 5.42 Cl 18.17 N3.59 fnd:C 64.45 H 5.40 Cl 17.89 N3.62

7. (+/−)-cis-8,9-Dimethoxy-6-(3,4-dimethoxyphenyl)-1,2,3,4,4a,10b-hexahydrophenanthridine M.p.: 160–162° C., yield 61.3% of theory

EF: $C_{23}H_{27}NO_4$; MW: 381.48

Elemental analysis: calc.: C 72.42 H 7.13 N 3.67 fnd: C 72.38 H 7.00 N 3.53

8. (+/−)-cis-8,9-Dimethoxy-2,3-dimethyl-6-(4-p-toluenesulfonamidophenyl)-1,4,4a,10b-tetrahydrophenanthridine M.p. from 128° C. (decomposition).

EF: $C_{30}H_{32}N_2O_4S$; MW: 516.66

Elemental analysis: (×0.5 H$_2$O): calc.: C 68.55 H 6.33 N 5.33 fnd: C 68.91 H 6.29 N 5.31

9. (+/−)-trans-8,9-Dimethoxy-6-(4-p-toluenesulfonamidophenyl)-1,2,3,4,4a,10b-hexahydrophenanthridine hydrochloride M.p.: 219–222° C., yield: 30.2% of theory EF: $C_{28}H_{30}N_2O_4S×HCl×H_2O$; MW: 545.1

Elemental analysis: calc.: C 61.70 H 6.10 Cl 6.50 N 5.14 S 5.88 fnd: C 61.94 H 6.00 Cl 6.79 N 5.15 S 5.83

10. (+/−)-trans-8,9-Dimethoxy-6-(4-p-toluenesulfonamidophenyl)-1,4,4a,10b-tetrahydrophenanthridine hydrochloride M.p.: 189–192° C., yield: 40.6% of theory EF: $C_{28}H_{28}N_2O_4S×HCl ×H_2O$; MW: 543.09

Elemental analysis: calc.: C 61.93 H 5.75 Cl 6.53 N 5.16 S 5.90 fnd: C 61.44 H 5.51 Cl 6.78 N 5.04 S 5.83

11. (+/−)-trans-8,9-Dimethoxy-2,3-dimethyl-6-(4-p-toluenesulfonamidophenyl)-1,4,4a,10b-tetrahydrophenanthridine M.p.: 200–203.5° C., yield: 54.2% of theory

EF: $C_{30}H_{32}N_2O_4S$; MW: 516.66

Elemental analysis: calc.: C 69.74 H 6.24 N 5.42 S 6.21 fnd: C 69.67 H 6.37 N 5.37 S 6.02

12. (+/−)-trans-8,9-Dimethoxy-1,4-ethano-6-(4-p-toluenesulfonamidophenyl)-1,2,3,4,4a,10b-hexahydrophenanthridine M.p.: >220° C. (decomposition).

EF: $C_{30}H_{32}N_2O_4S$; MW: 516.66

13. (+/−)-cis-6-(4-Acetoxyphenyl)-8,9-diethoxy-1,2,3,4,4a,10b-hexahydrophenanthridine M.p.: 99–101° C., yield: 31.3% of theory

EF: $C_{25}H_{29}NO_4$; MW: 407.51

Elemental analysis: calc.: C 73.69 H 7.17 N 3.44 fnd: C 73.47 H 7.15 N 3.47

14. (+/−)-cis-6-(4-Benzylphenyl)-8,9-diethoxy-1,2,3,4,4a,10b-hexahydrophenanthridine M.p.: 135–137° C., yield: 65.1% of theory

EF: $C_{30}H_{33}NO_2$; MW: 439.6

Elemental analysis: calc.: C 81.97 H 7.56 N 3.18 fnd: C 81.93 H 7.54 N 3.43

15. (+/−)-cis-6-Biphenyl-8,9-diethoxy-1,2,3,4,4a,10b-hexahydrophenanthridine

M.p.: 156–158° C., yield: 38.6% of theory

EF: $C_{29}H_{31}NO_2$; MW: 425.58

Elemental analysis: calc.: C 81.85 H 7.34 N 3.29 fnd: C81.69H7.34 N 3.17

16. (+/−)-cis-8,9-Diethoxy-6-(4-fluorophenyl)-1,2,3,4,4a,10b-hexahydrophenanthridine M.p.: 92–93° C., yield: 20.3% of theory

EF: $C_{23}H_{26}FNO_2$; MW: 367.47

Elemental analysis: calc.: C 75.18 H 7.13 N 3.81 fnd: C 75.21 H 7.19 N 3.74

17. (+/−)-cis-8,9-Diethoxy-7-(4-trifluoromethylphenyl)-1,2,3,4,4a,10b-hexahydrophenanthridine Oil, yield: 27.5% of theory

EF: $C_{24}H_{26}F_3NO_2$; MW: 417.48

Elemental analysis: calc.: C 69.05 H 6.28 N 3.36 fnd: C 68.70 H 6.31 N 3.09

18. (+/−)-cis-8,9-Diethoxy-6-(4-cyanophenyl)-1,2,3,4,4a,10b-hexahydrophenanthridine M.p.: 125–127° C., yield: 59.9% of theory

EF: $C_{24}H_{26}N_2O_2$; MW: 374.49

Elemental analysis: calc.: C 76.98 H 7.00 N 7.48 fnd: C 76.92 H 7.15 N 7.37

19. (+/−)-cis-8,9-Diethoxy-6-(4-trifluoromethoxyphenyl)-1,2,3,4a,10b-hexahydrophenanthridine M.p.: 98–100° C., yield: 23.4% of theory

EF: $C_{24}H_{26}F_3NO_3$; MW: 433.48

Elemental analysis: calc.: C 66.50 H 6.05 N 3.23 fnd: C 66.44 H 6.05 N 3.18

20. (+/−)-cis-9-Ethoxy-8-methoxy-6-(4-p-toluenesulfonamidophenyl)-1,2,3,4,4a,10b-hexahydrophenanthridine M.p.: 95° C. (dec.), yield: 51.0% of theory

EF: $C_{29}H_{32}N_2O_4S$; MW: 504.65

Elemental analysis: calc.: C 69.02 H 6.39 N 5.55 fnd: C 69.19 H 6.68 N 5.44

21. (+/−)-cis-9-Ethoxy-8-methoxy-6-(4-nitrophenyl)-1,2,3,4,4a,10b-hexahydrophenanthridine M.p.: 122–124° C., yield: 60.5% of theory

EF: $C_{22}H_{24}N_2O_4$; MW: 380.45

Elemental analysis: calc.: C 69.46 H 6.36 N 7.36 fnd: C 69.21 H 6.23 N 7.24

22. (+/−)-cis-9-Ethoxy-8-methoxy-6-(4-methanesulfonylphenyl)-1,2,3,4,4a,10b-hexahydrophenanthridine M.p.: 196–197° C., yield: 67.2% of theory

EF: $C_{23}H_{27}NO_4$; MW: 413.54

Elemental analysis: calc.: C 66.80 H 6.58 N 3.39 fnd: C 66.85 H 6.62 N 3.45

23. (+/−)-cis-9-Ethoxy-8-methoxy-6-[4-(4-methoxycarbonylphenyl)sulfonamidophenyl]-1,2,3,4,4a,10b-hexahydrophenanthridine hydrochloride M.p.: dec. from 210° C., yield: 55.6% of theory EF: $C_{30}H_{32}N_2O_6S \times HCl$; MW: 585.12

Elemental analysis $\times 0.5\ H_2O$: calc.: C 60.65 H 5.77 N 4.72 Cl 5.97 S 5.40 fnd: C 60.51 H 5.68 N 4.73 Cl 5.89 S 5.93

24. (+/−)-cis-8,9-Diethoxy-6-(pyrid-4-yl)-1,2,3,4,4a,10b-hexahydrophenanthridine dihydrochloride 3.2 g of (+/−)-cis-N-[2-(3,4-diethoxyphenyl)cyclohexyl]-4-isonicotinamide are dissolved in 50 ml of acetonitrile and 3.0 ml of phosphorus oxychloride and the solution is stirred at 50° C. for 8 h. The reaction mixture is added to 100 ml of saturated sodium hydrogencarbonate solution and extracted with ethyl acetate. The organic phase is washed with sodium hydrogencarbonate solution and water, dried using sodium sulfate and concentrated. The residue is chromatographed on silica gel using a mixture of toluene/dioxane/petroleum ether/triethylamine in the ratio 6:2:1:0.5. The product fractions are concentrated, the residue is dissolved in 30 ml of ethanol, and the solution is treated with 7 ml of diethyl ether saturated with hydrogen chloride gas and added dropwise to 400 ml of diethyl ether. The precipitate is filtered off with suction, washed with diethyl ether and dried. 1.6 g (43.4% of theory) of the title compound are obtained as the dihydrochloride of M.p.: 223° C. (dec.).

EF: $C_{22}H_{26}N_2O_2 \times 2\ HCl$; MW: 423.39

Elemental analysis: calc.: C 57.52 H 5.42 Cl 18.17 N 3.59 fnd: C 57.09 H 5.40 Cl 17.89 N 3.62

Starting from the starting compounds described below, the following are obtained according to the procedure as in Example 24:

25. (+/−)-cis-8,9-Diethoxy-6-(pyrid-3-yl)-1,2,3,4,4a,10b-hexahydrophenanthridine hydrochloride M.p.: 233° C., yield 37.8% of theory EF: $C_{22}H_{26}N_2O_2 \times HCl$; MW: 386.93

Elemental analysis: calc.: C 68.29 H 7.03 Cl 9.16 N 7.24 fnd: C 68.43 H 7.09 Cl 9.29 N 7.30

26. (+/−)-cis-8,9-Diethoxy-6-(2-chloropyrid-5-yl)-1,2,3,4,4a,10b-hexahydrophenanthridine The title compound is obtained by concentrating the product fractions after chromatography analogously to the procedure as in Example 24:

M.p.: 123–126° C., yield: 75.7% of theory

EF: $C_{22}H_{25}ClN_2O_2$; MW: 384.91

Elemental analysis: calc.:C 68.01 H 6.59 Cl 9.13 N 7.21 fnd: C 68.04 H 6.45 Cl 9.26 N 7.16

27. (+/−)-cis-8,9-Diethoxy-6-(2-hydroxypyrid-5-yl)-1,2,3,4,4a,10b-hexahydrophenanthridine 850 mg of (+/−)-cis-8,9-diethoxy-6-(2-chloropyrid-5-yl)-1,2,3,4,4a,10b-hexahydrophenanthridine are suspended in 60 ml of toluene, treated with 1.0 g of potassium carbonate, 2.0 g of potassium hydroxide and 0.26 mg of tris[2-(2-methoxyethoxy)ethyl]amine and refluxed overnight. The suspension is filtered, the solvent is removed in vacuo, the residue is taken up in water, and the mixture is neutralized with 0.1 M hydrochloric acid and extracted with ethyl acetate. The organic phase is dried using sodium sulfate, the solvent is removed in vacuo, and the precipitate which is deposited in the course of this is filtered off with suction and dried. M.p.: 211–213° C., yield 12.3% of theory.

EF: $C_{22}H_2N_2O_3$; MW: 366.46

Elemental analysis: calc.: C 72.11 H 7.15 N 7.64 fnd: C 72.55 H 7.10 N 7.58

28. (+/−)-cis-8,9-Dimethoxy-6-(4-aminophenyl)-1,2,3,4,4a,10b-hexahydrophenanthridine 8.5 g of (+/−)-cis-8,9-dimethoxy-6-(4-nitrophenyl)-1,2,3,4,4a,10b-hexahydrophenanthridine are dissolved in 200 ml of methanol, and the solution is treated with 5 ml of concentrated hydrochloric acid, 20 ml of water and 800 mg of iron powder and stirred overnight at RT. The reaction mixture is filtered, the filtrate is concentrated, the residue is extracted with sodium hydrogencarbonate solution/ethyl acetate, and the organic phase is dried using sodium sulfate and concentrated. The residue is chromatographed on silica gel using a mixture of toluene/dioxane/triethylamine in the ratio 40:20:2. After concentration of the corresponding eluate fractions, 5.5 g (70.5% of theory) of the title compound of m.p. 159.5–161° C. are obtained.

EF: $C_{21}H_{24}N_2O_2$; MW: 336.44

Starting from the starting compounds described below, the following is obtained according to the procedure as in Example 28:

29. (+/−)-cis-9-Ethoxy-8-methoxy-6-(4-aminophenyl)-1,2,3,4,4a,10b-hexahydrophenanthridine M.p.: 183–186° C., yield 30.8% of theory

EF: $C_{22}H_{26}N_2O_2$; MW: 350.47

Elemental analysis: calc.: C 75.40 H 7.48 N 7.99 fnd: C 75.72 H 7.53 N 7.70

30. (+/−)-cis-8,9-Dimethoxy-6-[4-bis(p-nitrophenylsulfonyl)aminophenyl]-1,2,3,4,4a,10b-hexahydrophenanthridine 1.45 g of 4-nitrobenzenesulfonyl chloride in 20 ml of methylene chloride are added dropwise to a solution of 2.0 g of (+/−)-cis-8,9-dimethoxy-6-(4-aminophenyl)-1,2,3,4,4a,10b-hexahydrophenanthridine in 50 ml of methylene chloride and 1.0 ml of triethylamine. The solution is stirred overnight at RT, extracted with water, and the organic phase is dried and concentrated. The residue is chromatographed on silica gel using a mixture of petroleum ether/ethyl acetate in the ratio 3:2. After concentration of the corresponding eluate fractions, the title compound of m.p. 234.5° C. is obtained.

EF: $C_{33}H_{30}N_4O_{10}S_2$; MW: 706.76

Elemental analysis: calc.: C 56.08 H 4.28 N 7.93 S 9.07 fnd: C 55.93 H 4.29 N 7.73 S 8.86

31. (+/−)-cis-8,9-Dimethoxy-6-(4-acetamidophenyl)-1,2,3,4,4a,10b-hexahydrophenanthridine 1.0 g of (+/−)-cis-8,9-dimethoxy-6-(4-aminophenyl)-1,2,3,4,4a,10b-hexahydrophenanthridine is suspended in 10 ml of acetic anhydride and the suspension is stirred at RT for 1 h. The solution is treated with diethyl ether, and the precipitate is filtered off with suction and extracted with sodium hydrogencarbonate solution/ethyl acetate. After drying and concentration of the organic phase, the residue is recrystallized from ethyl acetate/methanol. 0.63 g (56.0% of theory) of the title compound of m.p. 218° C. is obtained.

EF: $C_{23}H_{26}N_2O_3$; MW: 378.48

Elemental analysis: calc.: C 72.99 H 6.92 N 7.40 fnd: C 72.93 H 6.91 N 7.33

Starting from the starting compounds described below, the following is obtained according to the procedure as in Example 31:

32. (+/−)-cis-9-Ethoxy-8-methoxy-6-(4-acetamidophenyl)-1,2,3,4,4a,10b-hexahydrophenanthridine Solidifying oil, yield 69.7% of theory

EF: $C_{24}H_{28}N_2O_3$; MW 392.50

Elemental analysis: calc.: C 73.44 H 7.19 N 7.14 fnd: C 73.01 H 7.38 N 6.68

33. (+/−)-cis-8,9-Dimethoxy-6-[4-bis(p-toluenesulfonyl)aminophenyl]-1,2,3,4,4a,10b-hexahydrophenanthridine 2.0 g of (+/−)-cis-8,9-dimethoxy-6-(4-p-toluenesulfonamidophenyl)-1,2,3,4,4a,10b-hexahydrophenanthridine in 5 ml of dimethylformamide and then 1.0 g of p-toluenesulfonyl chloride in 5 ml of dimethylformamide are added dropwise to a suspension of 200 mg of 80% strength sodium hydride in 20 ml of dimethylformamide. After stirring at RT for 2 h, the mixture is added to ice-water and extracted with ethyl acetate/diethyl ether in the ratio 1:1. After drying and concentration of the organic phase, the residue is chromatographed on silica gel using a mixture of ethyl acetate/petroleum ether in the ratio 4:1. After concentration of the corresponding eluate fractions, the title compound of m.p. 120–130° C. is obtained.

EF: $C_{35}H_{36}N_2O_6S_2$; MW: 644.81

Elemental analysis: calc.: C 64.30 H 5.70 N 4.28 S 9.81 fnd: C 64.19 H 5.71 N 4.22 S 9.74

34. (+/−)-cis-8,9-Dimethoxy-6-[(N-acetyl-4-p-toluenesulfonamido)phenyl]-1,2,3,4,4a,10b-hexahydrophenanthridine 1.5 g of (+/−)-cis-8,9-dimethoxy-6-(4-p-toluenesulfonamidophenyl)-1,2,3,4,4a,10b-hexahydrophenanthridine in 5 ml of dimethylformamide and then 0.5 ml of acetyl chloride in 5 ml of dimethylformamide are added dropwise to a suspension of 100 mg of 80% strength sodium hydride in 10 ml of dimethylformamide. The mixture is stirred overnight at RT, added to sodium hydrogencarbonate solution and extracted with ethyl acetate. After drying and concentration of the organic phase, the residue is chromatographed on silica gel using a mixture of toluene/dioxane in the ratio 2:1. After concentration of the appropriate eluate fractions, the title compound of m.p. 212–216° C. is obtained.

EF: $C_{30}H_{32}N_2O_5S$; MW 532.66

Elemental analysis: calc.: C 67.65 H 6.06 N 5.26 S 6.02 fnd: C 67.71 H 6.03 N 5.21 S 5.83

Starting from the starting compounds described below, the following is obtained according to the procedure as in Example 34:

35. (+/−)-cis-8,9-Diethoxy-6-[(N-acetyl-4-p-toluenesulfonamido)phenyl]-1,2,3,4,4a,10b-hexahydrophenanthridine Solidified oil, yield 41.6% of theory

EF: $C_{32}H_{36}N_2O_5S$; MW 560.72

Elemental analysis: calc.: C 68.55 H 6.74 N 5.00 S 5.72 fnd: C 68.71 H 6.49 N 4.81 S 5.52

36. (+/−)-cis-9-Ethoxy-8-methoxy-6-[(N-methyl-4-p-toluenesulfonamido)phenyl]-1,2,3,4,4a,10b-hexahydrophenanthridine 60 mg of 80% strength sodium hydride are suspended in 10 ml of dimethylformamide under nitrogen, treated with 500 mg of (+/−)-cis-9-ethoxy-8-methoxy-6-(4-p-toluenesulfonamidophenyl)-1,2,3,4,4a,10b-hexahydrophenanthridine dissolved in 5 ml of dimethylformamide and 70 µl of methyl iodide dissolved in 5 ml of dimethylformamide and stirred overnight at RT. After hydrolysis with water, the mixture is extracted with diethyl ether and the organic phase is then dried using sodium sulfate and concentrated. The residue is chromatographed on silica gel using a mixture of petroleum ether/ethyl acetate/methanol in the ratio 6/3/1. After concentration of the corresponding eluate fractions, 150 mg (28.9% of theory) of the title compound are obtained as a solidifying oil.

EF: $C_{30}H_{34}N_2O_4S$; MW 518.68

Elemental analysis: calc.: C 68.29 H 6.69 N 5.31 S 6.08 fnd: C 68.84 H 6.69 N 5.32 S 6.07

37. (+/−)-cis-8,9-Diethoxy-6-(4-hydroxyphenyl)-1,2,3,4,4a,10b-hexahydrophenanthridine 2.68 g of (+/−)-cis-6-(4-acetoxyphenyl)-8,9-diethoxy-1,2,3,4,4a,10b-hexahydrophenanthridine are dissolved in 15 ml of methanol, treated with 1.1 g of potassium hydroxide and the mixture is stirred at RT for 2 h. After removal of the solvent in vacuo, the residue is taken up in water, rendered neutral and extracted with ethyl acetate. The organic phase is dried using sodium sulfate and the solvent is removed in vacuo. 1.23 g (51.2% of theory) of the title compound of m.p. 232–234° C. are obtained.

EF: $C_{23}H_{27}NO_3$; MW 365.48

Elemental analysis: (×0.6 $H_2O$):

calc.: C 73.42 H 7.55 N 3.72 fnd: C 73.51 H 7.39 N 3.79

Starting Compounds

A1. (+/−)-cis-N-[2-(3,4-Dimethoxyphenyl)cyclohexyl]-4-p-toluenesulfonamidobenzamide 6.4 g of (+/−)-cis-1,2-dimethoxy-4-(2-aminocyclohexyl)benzene are dissolved in 150 ml of methylene chloride and 9 ml of triethylamine. A solution of 11.2 g of 4-p-toluenesulfonamidobenzoyl chloride in 200 ml of methylene chloride is added dropwise at RT in the course of 3 h, and the mixture is extracted after stirring for 1 h with 100 ml each of water, 2N hydrochloric acid, satd. sodium hydrogencarbonate solution and water again. The organic phase is dried using sodium sulfate, concentrated and crystallized from ethyl acetate. 3.9 g (28.2% of theory) of the title compound of m.p. 174–176° C. are obtained.

Starting from the starting compounds described below, the following are obtained according to the procedure as in Example A1:

A2. (+/−)-cis-N-[2-(3,4-Diethoxyphenyl)cyclohexyl]4-p-toluenesulfonamidobenzamide Solidifying oil; yield 70.6% of theory.

A3. (+/−)-cis-N-[2-(3-Cyclopentyloxy-4-methoxyphenyl)cyclohexyl]-4-p-toluenesulfonamidobenzamide Oil; yield 71.6% of theory.

A4. (+/−)-cis-N-[2-(4-Cyclopentyloxy-3-methoxyphenylcyclohexyl]-4-p-toluenesulfonamidobenzamide M.p.: 90° C., yield 55.6% of theory.

A5. (+/−)-cis-N-[2-(3,4-Dimethoxyphenyl)cyclohexyl]-4-nitrobenzamide

M.p.: 122° C., yield 98.0% of theory.

A6. (+/−)-cis-N-[2-(3,4-Dimethoxyphenyl)cyclohexyl]-2,6-dichlorobenzamide

M.p.: 181–184.5° C., yield quantitative.

A7. (+/−)-cis-N-[2-(3,4-Dimethoxyphenyl)cyclohexyl]-3,4-dimethoxybenzamide

Oil, yield quantitative.

A8. (+/−)-cis-N-[2-(3,4-Dimethoxyphenyl)-4,5-dimethylcyclohex-4-enyl]-4-p-toluenesulfonamidobenzamide M.p.: 129–141° C., yield 31.5% of theory.

A9. (+/−)-trans-N-[2-(3,4-Dimethoxyphenyl)cyclohexyl]-4-p-toluenesulfonamidobenzamide M.p.: 214–220° C., yield 34.5% of theory.

A10. (+/−)-trans-N-[2-(3,4-Dimethoxyphenyl)cyclohex-4-enyl]-4-p-toluenesulfonamidobenzamide M.p.: 119–126° C., yield 93.5% of theory.

A11. (+/−)-trans-N-[2-(3,4-Dimethoxyphenyl)4,5-dimethylcyclohex-4-enyl]-4-p-toluenesulfonamidobenzamide M.p.: 139° C. (decomposition), yield 64.9% of theory.

A12. (+/−)-trans-N-[2-(3,4-Dimethoxyphenyl)-bicyclo[2.2.2]oct-2-yl-4-p-toluenesulfonamidobenzamide
Oil, yield 52.5% of theory.

A13. (+/−)-cis-N-[2-(3,4-Diethoxyphenyl)cyclohexyl]4-acetoxybenzamide
M.p.: 81–84° C., yield 75.8% of theory.

A14. (+/−)-cis-N-[2-(3,4-Diethoxyphenyl)cyclohexyl]-4-benzylbenzamide
M.p.: 146–150° C., yield 72.7% of theory.

A15. (+/−)-cis-N-[2-(3,4-Diethoxyphenyl)cyclohexyl]-4-phenylbenzamide
M.p.: 151–154° C., yield 48.0% of theory.

A16. (+/−)-cis-N-[2-(3,4-Diethoxyphenyl)cyclohexyl]-4-fluorobenzamide
M.p.: 149–150° C., yield 63.0% of theory.

A17. (+/−)-cis-N-[2-(3,4-Diethoxyphenylcyclohexyl]4-trifluoromethylbenzamide
M.p.: 155–156° C., yield 85.7% of theory.

A18. (+/−)-cis-N-[2-(3,4-Diethoxyphenyl)cyclohexyl]4-cyanobenzamide
M.p.: 165–167° C., yield 75.3% of theory.

A19. (+/−)-cis-N-[2-(3,4-Diethoxyphenyl)cyclohexl]-4-trifluoromethoxybenzamide
M.p.: 111–113.5° C., yield 38.9% of theory.

A20. (+/−)-cis-N-[2-(3-Ethoxy-4-methoxyphenyl)cyclohexyl]-4-p-toluenesulfonamidobenzamide
M.p.: 143–150° C., yield 60.7% of theory.

A21. (+/−)-cis-N-[2-(3-Ethoxy-4-methoxyphenyl)cyclohexyl]-4-nitrobenzamide
M.p.: 120–140° C., yield 89.0% of theory.

A22. (+/−)-cis-N-[2-(3-Ethoxy-4-methoxyphenyl)cyclohexyl]-4-methanesulfonylbenzamide
M.p.: 180–181° C., yield 75.3% of theory.

A23. (+/−)-cis-N-[2-(3-Ethoxy-4-methoxyphenyl)cyclohexyl]-4-(4-methoxycarbonylphenyl)sulfonamidobenzamide
M.p.: 176–182° C., yield 42.4% of theory.

A24. (+/−)-cis-N-[2-(3,4-Diethoxyphenyl)cyclohexyl]-4-isonicotinamide 2.5 g of (+/−)-cis-1,2-diethoxy-4-(2-aminocyclohexyl)benzene are dissolved in 30 ml of methylene chloride and 5 ml of triethylamine. A suspension of 2.0 g of isonicotinoyl chloride in 30 ml of methylene chloride is added dropwise at RT in the course of 3 h, and the mixture is extracted after stirring for 1 h with 50 ml each of water, 2N hydrochloric acid, satd. sodium hydrogencarbonate solution and water again. The organic phase is dried using sodium sulfate and concentrated, and the residue is chromatographed on silica gel using a mixture of toluene/dioxane/petroleum ether/triethylamine in the ratio 6:2:1:0.5. After concentration of the corresponding eluates, 3.44 g (98.3% of theory) of the title compound are obtained as a solidifying oil.

Starting from the starting compounds described below, the following are obtained according to the procedure as in Example A24:

A25. (+/−)-cis-N-[2-(3,4-Diethoxyphenyl)cyclohexyl]-4-nicotinamide
Solidifying oil; yield quantitative.

A26. (+/−)-cis-N-[2-(3,4-Diethoxyphenyl)cyclohexyl]-6-chloronicotinamide
Oil; yield 59.0% of theory.

B1. (+/−)-cis-1,2-Dimethoxy-4-(2-aminocyclohexyl)benzene 8.5 g of (+/−)-cis-1,2-dimethoxy-4-(2-nitrocyclohexyl)benzene are dissolved in 400 ml of methanol and treated in portions with 7 ml of hydrazine hydrate and 2.5 g of Raney nickel at RT in the course of 8 h. After stirring overnight at RT, the reaction mixture is filtered, the filtrate is concentrated and the residue is chromatographed on silica gel using a mixture of toluene/ethyl acetate/triethylamine=(4:2:0.5).
Oil; yield 74.4% of theory.

Starting from the starting compounds described below, the following are obtained according to the procedure as in Example B1:

B2. (+/−)-cis-1,2-Diethoxy-4-(2-aminocyclohexyl)benzene
Oil; yield 42.8% of theory.

B3. (+/−)-cis-2-Cyclopentyloxy-1-methoxy-4-(2-aminocyclohexyl)benzene
Oil; yield 68.2% of theory.

B4. (+/−)-cis-1-Cyclopentyloxy-2-methoxy-4-(2-aminocyclohexyl)benzene
Oil; yield 69.0% of theory.

B5. (+/−)-cis-1,2-Dimethoxy4-(2-amino-4,5-dimethylcyclohex-4-enyl)benzene
Oil; yield 87.3% of theory.

B6. (+/−)-trans-1,2-Dimethoxy-4-(2-aminocyclohexyl)benzene
Oil; yield 65.9% of theory.

B7. (+/−)-trans-1,2-Dimethoxy-4-(2-aminocyclohex-4-enyl)benzene
Oil; yield 28.9% of theory.

B8. (+/−)-trans-1,2-Dimethoxy-4-(2-amino-4,5-dimethylcyclohex-4-enyl)benzene
Solidified oil, yield 94% of theory.

B9. (+/−)-trans-3-(3,4-Dimethoxyphenyl)-bicyclo[2.2.2]oct-2-ylamine
Oil, yield 70.7% of theory.

B10. (+/−)-cis-2-Ethoxy-1-methoxy-4-(2-aminocyclohexyl)benzene 40.0 g of (+/−)-cis-2-ethoxy-1-methoxy-4-(2-nitrocyclohex-4-enyl)benzene are dissolved in 1000 ml of ethanol and 500 ml of tetrahydrofuran, treated with 10 g of Raney nickel and hydrogenated at RT in an autoclave for 4 days at a hydrogen pressure of 100 bar. After filtration and removal of the solvent in vacuo, 35.9 g (99.8% of theory) of the title compound are obtained as a solidifying oil.

C1. (+/−)-cis-1,2-Dimethoxy-4-(2-nitrocyclohexyl)benzene 8.4 g of (+/−)-cis-1,2-dimethoxy-4-(2-nitrocyclohex-4-enyl)benzene are dissolved in 450 ml of methanol, treated with 2 ml of conc. hydrochloric acid and hydrogenated after addition of 500 mg of Pd/C 10% strength. The reaction mixture is filtered and the filtrate is concentrated. M.p.: 84–86.5° C.; yield quantitative.

Starting from the starting compounds described below, the following are obtained according to the procedure as in Example C1:

C2. (+/−)-cis-1,2-Diethoxy-4-(2-nitrocyclohexyl)benzene
Oil; yield 96.5% of theory.

C3. (+/−)-cis-2-Cyclopentyloxy-1-methoxy-4-(2-nitrocyclohexyl)benzene
M.p.: 107.5° C., yield 53.5% of theory.

C4. (+/−)-cis-1 -Cyclopentyloxy-2-methoxy-4-(2-nitrocyclohexyl)benzene
M.p.: 92–94.5° C., yield 74.8% of theory.

C5. (+/−)-trans-1,2-Dimethoxy-4-(2-nitrocyclohexyl)benzene
Oil; yield 47.0% of theory.

C6. (+/−)-trans-3-(3,4-Dimethoxyphenyl)-2-nitrobicyclo[2.2.2]octane
Oil, yield 76.0% of theory.

D1. (+/−)-cis-1,2-Dimethoxy-4-(2-nitrocyclohex-4-enyl)benzene 10.0 g of (+/−)-trans-1,2-dimethoxy-4-(2-nitrocyclohex-4-enyl)benzene and 20.0 g of potassium hydroxide are dissolved in 150 ml of ethanol and 35 ml of dimethylformamide. A solution of 17.5 ml of conc. sulfuric acid in 60 ml of ethanol is then added dropwise such that the internal temperature does not exceed 4° C. After stirring for 1 h, the mixture is added to 1 l of ice-water, the precipitate is filtered off with suction, washed with water and dried and the crude product is recrystallized from ethanol. M.p.: 82.5–84° C.; yield 86% of theory.

Starting from the starting compounds described below, the following are obtained according to the procedure as in Example D1:

D2. (+/−)-cis-1,2-Diethoxy-4-(2-nitrocyclohex4-enyl)benzene
   Oil; yield 96.5% of theory.

D3. (+/−)-cis-2-Cyclopentyloxy-1-methoxy-4-(2-nitrocyclohex-4-enyl)benzene
   M.p.: 78–81° C., yield 89.2% of theory.

D4. (+/−)-cis-1-Cyclopentyloxy-2-methoxy-4-(2-nitrocyclohex-4-enyl)benzene
   M.p.: 81.5–85° C., yield quantitative.

D5. (+/−)-cis-2-Diethoxy-1-methoxy-4-(2-nitrocyclohex-4-enyl)benzene
   M.p.: 66.67° C., yield 97.2% of theory.

D6. (+/−)-cis-2-Dimethoxy-4-(4,5-dimethyl-2-nitrocyclohex-4-enyl)benzene
   M.p.: 97.5° C., yield 91.8% of theory.

E1. (+/−)-trans-1,2-Dimethoxy-4-(2-nitrocyclohex-4-enyl)benzene 50.0 g of 3,4-dimethoxy-ω-nitrostyrene and 1.0 g (9.1 mmol) of hydroquinone are suspended in 200 ml of abs. toluene and treated at −70° C. with 55.0 g (1.02 mol) of liquid 1,3-butadiene. The mixture is stirred at 160° C. for 6 days in an autoclave and then cooled. Some of the solvent is distilled off in vacuo, and the resulting precipitate is filtered off with suction and recrystallized in ethanol. M.p.: 113.5–115.5° C.; yield 76.3% of theory.

Starting from the starting compounds described below, the following are obtained according to the procedure as in Example E1:

E2. (+/−)-trans-1,2-Diethoxy4-(2-nitrocyclohex-4-enyl)benzene
   M.p.: 80–81.5° C.; yield 59.8% of theory.

E3. (+/−)-trans-2-Cyclopentyloxy-1-methoxy-4-(2-nitrocyclohex-4-enyl)benzene
   M.p.: 135–136° C.; yield 77.7% of theory.

E4. (+/−)-trans-1-Cyclopentyloxy-2-methoxy-4-(2-nitrocyclohex-4-enyl)benzene
   M.p.: 109° C.; yield 71.1% of theory.

E5. (+/−)-trans-2-Ethoxy-1-methoxy-4-(2-nitrocyclohex-4-enyl)benzene
   M.p.: 129–130° C.; yield 75.7% of theory.

E6. (+/−)-trans-1,2-Dimethoxy-4-(4,5-dimethyl-2-nitrocyclohex-4-enyl)benzene
   M.p.: 131.5° C.; yield 79.3% of theory.

E7. (+/−)-trans-5-(3,4-Dimethoxyphenyl)-6-nitrobicyclo[2.2.2]oct-2-ene
   Oil, yield quantitative.

F1. 3,4-Dimethoxy-ω-nitrostyrene
   207.0 g of 3,4-dimethoxybenzaldehyde, 100.0 g of ammonium acetate and 125 ml of nitromethane are heated to boiling for 3–4 h in 1.0 l of glacial acetic acid. After cooling in an ice-bath, the precipitate is filtered off with suction, rinsed with glacial acetic acid and petroleum ether and dried. M.p.: 140–141° C. Yield: 179.0 g (68.5% of theory).

Starting from corresponding starting compounds of the formula VII, the following are obtained analogously to the procedure as in Example F1:

F2. 3,4-Diethoxy-ω-nitrostyrene
   M.p.: 136–136.5° C.; yield: 76.2% of theory.

F3. 3-Cyclopentyloxy-4-methoxy-ω-nitrostyrene
   M.p.: 137–138° C.; yield: 86.6% of theory.

F4. 4-Cyclopentyloxy-3-methoxy-ω-nitrostyrene
   M.p.: 90–91° C.; yield: 44.0% of theory.

F5. 3-Ethoxy-4-methoxy-ω-nitrostyrene
   M.p.: 132–133° C.; yield: 70.3% of theory.

Commercial Utility

The compounds according to the invention have valuable pharmacological properties which make them commercially utilizable. As selective cyclic nucleotide phosphodiesterase (PDE) inhibitors (mainly of type IV), they are suitable on the one hand as bronchial therapeutics (for the treatment of airway obstructions on account of their dilating but also on account of their respiratory rate- and respiratory drive-increasing action) and for the elimination of erectile dysfunction on account of the vasodilating action, but on the other hand especially for the treatment of disorders, in particular of inflammatory nature, e.g. of the airways (asthma prophylaxis), of the skin, of the intestine, of the eyes, of the central nervous system and of the joints, which are mediated by mediators, such as histamine, PAF (platelet-activating factor), arachidonic acid derivatives, such as leukotrienes and prostagalndins, cytokines, interleukins, chemokines, alpha-, beta- and gamma-interferon, tumor necrosis factor (TNF) or oxygen free radicals and proteases. In this case, the compounds according to the invention are distinguished by a low toxicity, a good enteral absorption (high bioavailability), a large therapeutic breadth and the absence of significant side effects.

On account of their PDE-inhibiting properties, the compounds according to the invention can be employed as therapeutics in human and veterinary medicine, where they can be used, for example, for the treatment and prophylaxis of the following diseases: acute and chronic (in particular inflammatory and allergen-induced) airway disorders of various origins (bronchitis, allergic bronchitis, bronchial asthma); dermatoses (especially of proliferative, inflammatory and allergic type), such as psoriasis (vulgaris), toxic and allergic contact eczema, atopic eczema, seborrheic eczema, lichen simplex, sunburn, pruritus in the anogenital area, alopecia areata, hypertrophic scars, discoid lupus erythematosus, follicular and wide-area pyodermias, endogenous and exogenous acne, acne rosacea and other proliferative, inflammatory and allergic skin disorders; disorders which are based on an excessive release of TNF and leukotrienes, thus, for example, disorders of the arthritis type (rheumatoid arthritis, rheumatoid spondylitis, osteoarthritis and other arthritic conditions), disorders of the immune system (AIDS, multiple sclerosis), types of shock [septic shock, endotoxin shock, gram-negative sepsis, toxic shock syndrome and ARDS (adult respiratory distress syndrome)] as well as generalized inflammations in the gastrointestinal area (Crohn's disease and ulcerative colitis); disorders which are based on allergic and/or chronic, abnormal immunological reactions in the area of the upper airways (pharynx, nose) and the adjacent regions (paranasal sinuses, eyes), such as allergic rhinitis/sinusitis, chronic rhinitis/sinusitis, allergic conjunctivitis and nasal polyps; but also disorders of the heart which can be treated by PDE inhibitors, such as cardiac insufficiency, or disorders which can be treated on account of the tissue-relaxant action of the PDE inhibitors, such as, for example, erectile dysfunction or colics of the kidneys and of the ureters in connection with kidney stones.

The invention further relates to a procedure for the treatment of mammals including humans who are suffering from one of the abovementioned illnesses. The process comprises administering to the sick mammal a therapeutically efficacious and pharmacologically tolerable amount of one or more of the compounds according to the invention.

The invention further relates to the compounds according to the invention for use in the treatment and/or prophylaxis of the illnesses mentioned.

The invention likewise relates to the use of the compounds according to the invention for the production of medicaments which are employed for the treatment and/or prophylaxis of the illnesses mentioned.

Medicaments for the treatment and/or prophylaxis of the illnesses mentioned which contain one or more of the compounds according to the invention are furthermore a subject of the invention.

The medicaments are prepared by processes known per se and familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar on the basis of his expert knowledge with the auxiliaries which are suitable for the desired pharmaceutical formulations. In addition to solvents, gel-forming agents, ointment bases and other active compound excipients, it is possible to use, for example, antioxidants, dispersants, emulsifiers, preservatives, solubilizers or permeation promoters.

For the treatment of disorders of the respiratory tracts, the compounds according to the invention are preferably also administered by inhalation. For this purpose, these are either administered directly as a powder (preferably in micronized form) or by atomization of solutions or suspensions which contain them. With respect to the preparations and administration forms, reference is made, for example, to the embodiments in European Patent 163 965.

For the treatment of dermatoses, the compounds according to the invention are administered, in particular, in the form of those medicaments which are suitable for topical application. For the production of the medicaments, the compounds according to the invention (=active compounds) are preferably mixed with suitable pharmaceutical auxiliaries and processed further to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by processes known per se. The active compounds are administered in the order of magnitude customary for PDE inhibitors. Thus topical application forms (such as ointments) for the treatment of dermatoses contain the active compounds in a concentration of, for example, 0.1–99%. The dose for administration by inhalation is customarily between 0.01 and 1 mg per burst of spray. The customary dose in the case of systemic therapy p.o. or i.v. is between 0.1 and 200 mg per administration.

Biological Investigations

In the investigation of PDE IV inhibition at the cellular level, the activation of inflammatory cells is of particular importance. An example which may be mentioned is the FMLP (N-formylmethionylleucylphenylalanine)-induced superoxide production of neutrophilic granulocytes, which can be measured as luminol-potentiated chemoluminescence [Mc Phail L C, Strum S L, Leone P A and Sozzani S, The neutrophil respiratory burst mechanism. In "Immunology Series" 1992, 57, 47–76; ed. Coffey R G (Marcel Decker, Inc., New York-Basle-Hong Kong)].

Substances which inhibit chemoluminescence and cytokine secretion and the secretion of proinflammatory mediators on inflammatory cells, in particular neutrophilic and eosinophilic granulocytes, T lymphocytes, monocytes and macrophages, are those which inhibit PDE IV. This isoenzyme of the phosphodiesterase families is particularly represented in granulocytes. Its inhibition leads to the increase of the intracellular cyclic AMP concentration and thus to the inhibition of cellular activation. PDE IV inhibition by the substances according to the invention is thus a central indicator of the suppression of inflammatory processes. (Giembycz M A, Could isoenzyme-selective phosphodiesterase inhibitors render bronchodilatory therapy redundant in the treatment of bronchial asthma? Biochem Pharmacol 1992, 43, 2041–2051; Torphy T J et al., Phosphodiesterase inhibitors: new opportunities for treatment of asthma. Thorax 1991, 46, 512–523; Schudt C et al., Zardaverine: a cyclic AMP PDE III/IV inhibitor. In "New Drugs for Asthma Therapy", 379–402, Birkhäuser Verlag Basle 1991; Schudt C et al., Influence of selective phosphodiesterase inhibitors on human neutrophil functions and levels of cAMP and $Ca_i$. Naunyn-Schmiedeberg's Arch Pharmacol 1991, 344, 682–690; Nielson C P et al., Effects of selective phosphodiesterase inhibitors on polymorphonuclear leukocyte respiratory burst. J Allergy Clin Immunol 1990, 86, 801–808; Schade et al., The specific type III and IV phosphodiesterase inhibitor zardaverine suppress formation of tumor necrosis factor by macrophages. European Journal of Pharmacology 1993, 230, 9–14).

1. Inhibition of PDE IV Activity

Methodology

The activity test was carried out according to the method of Bauer and Schwabe, which was adapted to microtiter plates (Naunyn-Schmiedeberg's Arch. Pharmacol. 1980, 311, 193–198). In this test, the PDE reaction is carried out in the first step. In a second step the resulting 5'-nucleotide is cleaved to give the uncharged nucleoside by means of a 5'-nucleotidase of the snake venom from *Crotalus atrox*. In the third step, the nucleoside is separated from the remaining charged substrate on ion-exchange columns. Using 2 ml of 30 mM ammonium formate (pH 6.0), the columns are eluted directly into minivials, to which 2 ml of scintillator fluid is additionally added for counting.

The inhibitory values determined for the compounds according to the invention follow from the following Table A, in which the numbers of the compounds correspond to the numbers of the examples.

TABLE A

| Inhibition of the PDE IV activity | |
|---|---|
| Compound | -log $IC_{50}$ |
| 1 | 7.73 |
| 2 | 8.39 |
| 3 | 7.76 |

TABLE A-continued

Inhibition of the PDE IV activity

| Compound | -log IC$_{50}$ |
|---|---|
| 4 | 6.12 |
| 5 | 7.22 |
| 6 | 6.77 |
| 7 | 6.44 |
| 8 | 6.91 |
| 9 | 6.17 |
| 10 | 6.10 |
| 12 | 5.77 |
| 13 | 8.43 |
| 14 | 8.08 |
| 15 | 7.98 |
| 16 | 7.93 |
| 17 | 8.00 |
| 18 | 8.24 |
| 19 | 7.97 |
| 20 | 9.05 |
| 21 | 8.46 |
| 22 | 8.66 |
| 23 | 8.70 |
| 24 | 8.08 |
| 25 | 7.96 |
| 26 | 8.41 |
| 27 | 6.66 |
| 29 | 7.69 |
| 30 | 7.36 |
| 31 | 7.30 |
| 32 | 8.38 |
| 33 | 7.27 |
| 34 | 7.42 |
| 35 | 7.81 |
| 36 | 9.09 |
| 37 | 8.04 |

What is claimed is:

1. A compound of Formula I

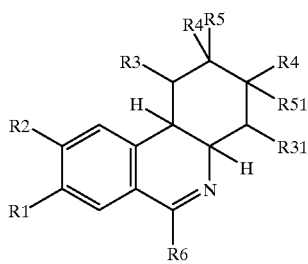

(I)

in which

R1 is hydroxyl, 1–4C-alkoxy, 3–7C-cycloalkoxy, 3–7C-cycloalkylmethoxy or 1–4C-alkoxy which is completely or partially substituted by fluorine, R2 is hydroxyl, 1–4C-alkoxy, 3–7C-cycloalkoxy, 3–7C-cycloalkylmethoxy or 1–4C-alkoxy which is completely or partially substituted by fluorine, or in which R1 and R2 together are a 1–2C-alkylenedioxy group, R3 is hydrogen or 1–4C-alkyl, R31 is hydrogen or 1–4C-alkyl, or in which R3 and R31 together are a 1–4C-alkylene group, R4 is hydrogen or 1–4C-alkyl, R5 is hydrogen, R51 is hydrogen, or in which R5 and R51 together are an additional bond, R6 is a pyridyl radical which is substituted by R61 or a phenyl radical which is substituted by R7 and R8, where R61 is hydrogen, hydroxyl, halogen, 1–4C-alkoxy, 1–4C-alkyl, carboxyl, trifluoromethyl, 1–4C-alkoxycarbonyl or 1–4C-alkoxy which is completely or partially substituted by fluorine, R7 is hydroxyl, halogen, cyano, 1–4C-alkyl, 1–4C-alkoxy, 1–4C-alkylcarbonyloxy, trifluoromethyl, phenyl, phenyl-1–4C-alkyl, nitro, amino, 1–4C-alkoxy which is completely or partially substituted by fluorine, or is SO$_2$-R70 or N(R71)R72, where R70 is 1–4C-alkyl, R71 is hydrogen, 1–4C-alkyl, SO$_2$-R9 or SO$_2$-R10 and R72 is 1–4C-alkyl, 1–4C-alkylcarbonyl or SO$_2$-R10, R8 is hydrogen, hydroxyl, halogen, 1–4C-alkoxy or 1–4C-alkyl and where R9 and R10 independently of one another are 1–4C-alkyl, phenyl, phenyl-1–4C-alkyl or phenyl which is substituted by one or more identical or different substituents, where the substituents are selected from the group consisting of nitro, 1–4C-alkyl, halogen, 1–4C-alkylcarbonylamino, 1–4C-alkoxy, 1–4C-alkoxy which is completely or partially substituted by fluorine, cyano, phenyl, naphthyl, trifluoromethyl and 1–4C-alkoxycarbonyl, or a salt thereof.

2. A compound of formula I as claimed in claim 1, in which

R1 is hydroxyl, 1–4C-alkoxy, 3–7C-cycloalkoxy, 3–7C-cycloalkylmethoxy or 1–4C-alkoxy which is completely or partially substituted by fluorine, R2 is hydroxyl, 1–4C-alkoxy, 3–7C-cycloalkoxy, 3–7C-cycloalkylmethoxy or 1–4C-alkoxy which is completely or partially substituted by fluorine, or in which R1 and R2 together are a 1–2C-alkylenedioxy group, R3 is hydrogen or 1–4C-alkyl, R31 is hydrogen or 1–4C-alkyl, or in which R3 and R31 together are a 1–4C-alkylene group, R4 is hydrogen or 1–4C-alkyl, R5 is hydrogen, R51 is hydrogen, or in which R5 and R51 together are an additional bond, R6 is a pyridyl radical which is substituted by R61, where R61 is hydrogen, hydroxyl, halogen, 1–4C-alkoxy, 1–4C-alkyl, carboxyl, trifluoromethyl, 1–4C-alkoxycarbonyl or 1–4C-alkoxy which is completely or partially substituted by fluorine, or a salt thereof.

3. A compound of formula I as claimed in claim 1, in which

R1 is hydroxyl, 1–4C-alkoxy, 3–7C-cycloalkoxy, 3–7C-cycloalkylmethoxy or 1–4C-alkoxy which is completely or partially substituted by fluorine, R2 is hydroxyl, 1–4C-alkoxy, 3–7C-cycloalkoxy, 3–7C-cycloalkylmethoxy or 1–4C-alkoxy which is completely or partially substituted by fluorine,
or in which
R1 and R2 together are a 1–2C-alkylenedioxy group,
R3 is hydrogen or 1–4C-alkyl,
R31 is hydrogen or 1–4C-alkyl,
or in which
R3 and R31 together are a 1–4C-alkylene group,
R4 is hydrogen or 1–4C-alkyl,
R5 is hydrogen,
R51 is hydrogen,
or in which
R5 and R51 together are an additional bond,
R6 is a phenyl radical which is substituted by R7 and R8, where
R7 is hydroxyl, halogen, cyano, 1–4C-alkyl, 1–4C-alkoxy, 1–4C-alkylcarbonyloxy, trifluoromethyl, phenyl, phenyl-1–4C-alkyl, nitro, amino or N(R71)R72, where
R71 is hydrogen, 1–4C-alkyl, SO$_2$-R9 or SO$_2$-R10 and
R72 is 1–4C-alkyl, 1–4C-alkylcarbonyl or SO$_2$-R10,
R8 is hydrogen, hydroxyl, halogen, 1–4C-alkoxy or 1–4C-alkyl
and where
R9 and R10 independently of one another are 1–4C-alkyl, phenyl, phenyl-1–4C-alkyl or phenyl which is substituted by one or more identical or different substituents, the substituents being selected from the group consisting of nitro, 1–4C-alkyl, halogen, 1–4C-alkylcarbonylamino, 1–4C-alkoxy, 1–4C-alkoxy completely or partially substituted by fluorine, cyano, phenyl, naphthyl and trifluoromethyl,
or a salt thereof.

4. A compound of formula I as claimed in claim 1, in which
R1 is hydroxyl, 1–4C-alkoxy, 3–7C-cycloalkoxy, 3–7C-cycloalkylmethoxy or 1–4C-alkoxy which is completely or partially substituted by fluorine,
R2 is hydroxyl, 1–4C-alkoxy, 3–7C-cycloalkoxy, 3–7C-cycloalkylmethoxy or 1–4C-alkoxy which is completely or partially substituted by fluorine,
or in which
R1 and R2 together are a 1–2C-alkylenedioxy group,
R3 is hydrogen or 1–4C-alkyl,
R31 is hydrogen or 1–4C-alkyl,
or in which
R3 and R31 together are a 1–4C-alkylene group,
R4 is hydrogen or 1–4C-alkyl,
R5 is hydrogen,
R51 is hydrogen,
or in which
R5 and R51 together are an additional bond,
R6 is a phenyl radical which is substituted by R7 and R8, where
R7 is hydroxyl, halogen, cyano, 1–4C-alkyl, 1–4C-alkoxy, 1–4C-alkylcarbonyloxy, trifluoromethyl, phenyl, phenyl-1–4C-alkyl, nitro, amino, 1–4C-alkoxy which is completely or partially substituted by fluorine, or is SO$_2$-R70 or N(R71)R72, where
R70 is 1–4C-alkyl,
R71 is hydrogen, 1–4C-alkyl, SO$_2$-R9 or SO$_2$-R10 and
R72 is 1–4C-alkyl, 1–4C-alkylcarbonyl or SO$_2$-R10,
R8 is hydrogen, hydroxyl, halogen, 1–4C-alkoxy or 1–4C-alkyl and where
R$_9$ and R$_{10}$ independently of one another are 1–4C-alkyl, phenyl, phenyl-1–4C-alkyl or phenyl which is substituted by one or more identical or different substituents, the substituents being selected from the group consisting of nitro, 1–4C-alkyl, halogen, 1–4C-alkylcarbonylamino, 1–4C-alkoxy, 1–4C-alkoxy which is completely or partially substituted by fluorine, cyano, phenyl, naphthyl, trifluoromethyl and 1–4C-alkoxycarbonyl,
or a salt thereof.

5. A compound of formula I as claimed in claim 1, in which
R1 is 1–4C-alkoxy or 3–7C-cycloalkoxy,
R2 is 1–4C-alkoxy or 3–7C-cycloalkoxy,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is a phenyl radical which is substituted by R7 and R8, where
R7 is hydroxyl, halogen, cyano, 1–4C-alkoxy, 1–4C-alkylcarbonyloxy, trifluoromethyl, phenyl, phenyl-1–4C-alkyl, nitro, amino, 1–4C-alkoxy which is completely or partially substituted by fluorine, or is SO$_2$-R70 or N(R71)R72, where
R70 is 1–4C-alkyl,
R71 is hydrogen, 1–4C-alkyl or SO$_2$-R10 and
R72 is 1–4C-alkylcarbonyl or SO$_2$-R10,
R8 is hydrogen, halogen or 1–4C-alkoxy
and where
R10 is phenyl which is substituted by a substituent, the substituent being selected from the group consisting of nitro, 1–4C-alkyl and 1–4C-alkoxycarbonyl,
or a salt thereof.

6. A medicament composition comprising an effective amount of at least one compound of the formula I as claimed in claim 1 together with pharmaceutical auxiliaries and/or excipients.

7. A method for treating or for prophylaxis of a disorder selected from the group consisting of an acute or chronic airway disorder, a dermatosis, a disorder based on an excessive release of TNF and leukotrienes, a disorder of the immune system, a type of shock, ARDS, generalized inflammation in the gastrointestinal area, a disorder based on allergic and/or chronic abnormal reaction in the upper airways area or in adjacent regions, a heart disorder which can be treated by a PDE inhibitor, and a disorder which can be treated which comprises the tissue-relaxant action of a PDE inhibitor, by administering an effective amount of an active ingredient to a mammal prone to or afflicted with such disorder, and wherein the active ingredient is a compound of claim 1 or a pharmacologically-acceptable salt thereof.

8. A process for treating a condition amenable to treatment with a PDE inhibitor which comprises administering an effective amount of the PDE inhibitor to a mammal in need of such therapy, and wherein the PDE inhibitor is a compound of formula I as claimed in claim 1, or a pharmacologically acceptable salt thereof.

9. A method for treating a disorder of the respiratory tract amenable to treatment with an active component, which comprises administering an effective amount of the active component to a mammal in need of such therapy, and wherein the active component is a compound of formula I as claimed in claim 1, or a pharmacologically acceptable salt thereof.

10. A method for treating a dermatosis amenable to treatment with an active component which comprises administering to a mammal in need of such therapy an effective amount of the active component, and wherein the active component is a compound of formula I as claimed in claim 1, or a pharmacologically acceptable salt thereof.

11. A method of compounding a medicament by combining an active component for treating an airway disorder with a suitable carrier therefor, and wherein the active component is a compound of formula I as claimed in claim 1 or a pharmacologically acceptable salt thereof.

12. A compound of formula I as claimed in claim 1 wherein R1 is hydroxyl, 1–4C-alkoxy, 3–7C-cycloalkoxy, 3–7C-cycloalkylmethoxy or 1–4C-alkoxy which is completely or partially substituted by fluorine, or a salt thereof.

\* \* \* \* \*